United States Patent [19]

Yamabe et al.

[11] 4,101,667
[45] Jul. 18, 1978

[54] BENZO[B,F]THIEPIN DERIVATIVES

[75] Inventors: Shigeru Yamabe, Kobe; Yasuo Fujimoto, Tokyo; Shoji Ryu, Noda; Yoshio Suzuki, Misato; Yoshihiro Tanaka, Soka; Toru Yamanaka; Kiyosato Nyu, both of Misato, all of Japan

[73] Assignee: Nippon Chemiphar Co., Ltd., Tokyo, Japan

[21] Appl. No.: 689,908

[22] Filed: May 25, 1976

[30] Foreign Application Priority Data

May 30, 1975 [GB] United Kingdom ............... 23703/75
Oct. 28, 1975 [JP] Japan ................. 50-129490

[51] Int. Cl.² ................... A61K 31/38; A61K 31/495; C07D 337/14; C07D 409/10
[52] U.S. Cl. ............................. 424/275; 260/293.57; 260/327 B; 424/250; 424/267; 544/375
[58] Field of Search ...................... 260/327 B; 424/275

[56] References Cited

U.S. PATENT DOCUMENTS 3,639,612 2/1972 DeLong et al. .............. 424/276
3,723,466 3/1973 Malen et al. .............. 260/333

OTHER PUBLICATIONS

Jilek et al., Chem. Abs. 73:109723w (1970).
Chemical Abstracts, Subject Index, Part 3, Chemical Substance Index A–D, vol. 76 (1972), p. 1270 cs.

*Primary Examiner*—Richard L. Raymond
*Attorney, Agent, or Firm*—Oblon, Fisher, Spivak, McClelland & Maier

[57] ABSTRACT

Dihydrodibenzo[b,f]thiepin compounds of formula (I) and process for making them. These compounds have antiinflammatory action.

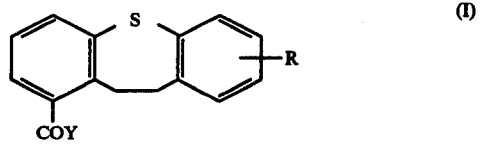

wherein R represents a hydrogen, fluorine atom, a trifluoromethyl, 1–5C lower alkoxy, hydroxy, hydroxyethoxy, aminoethoxy group or the group of the formula $-OCH_2CH_2OCH_2CH_2OH$, Y represents a hydroxy group or the group of the formula

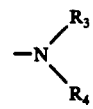

($R_3$ and $R_4$ represent a 1–4C lower alkyl group or $R_3$ and $R_4$ may jointly form a heterocyclic group together with an adjacent nitrogen atom.

16 Claims, No Drawings

BENZO[B,F]THIEPIN DERIVATIVES

This invention relates to novel benzo[b,f] thiepin derivatives and to a process for producing the same.

This invention further relates to an intermediate compound which is useful in the preparation of said compounds.

The present inventors have examined a wide variety of benzo[b,f] thiepin type compounds and, as a result, found that benzo[b,f] thiepin derivatives of the formula (I) exhibit an extremely excellent antiinflammatory action:

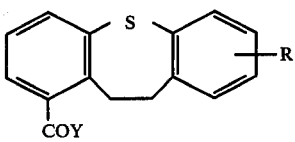
(I)

wherein R represents a hydrogen or fluorine atom, or a trifluoromethyl, 1–5C lower alkoxy, hydroxy, hydroxyethoxy, aminoethoxy group, or the group of the formula —OCH$_2$CH$_2$OCH$_2$CH$_2$OH, Y represents a hydroxy group or the group of the formula

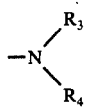

($R_3$ and $R_4$ represent a 1–4C lower alkyl group or $R_3$ and $R_4$ may jointly form a heterocyclic group together with an adjacent nitrogen atom).

It is, therefore, one object of this invention to provide novel benzo[b,f] thiepin derivatives represented by the formula (I).

It is another object of this invention to provide benzo[b,f] thiepin derivatives of the formula (I) possessing a strong antiflammatory action and presenting fewer adverse reactions.

It is a further object of this invention to provide a novel process for producing benzo[b,f] thiepin derivatives of the formula It is a further another object of this invention to provide an intermediate compound which is useful in the preparation of benzo[b,f] thiepin derivatives of the formula (I).

In the compound of the formula (I), the group represented by R can be substituted at any one of 2-, 3- or 4-position of the benzo[b,f] thiepin ring.

According to the present invention, the benzo[b,f]-thiepin derivatives of the formula (I) are produced according to any one of processes as shown below.

Process 1:

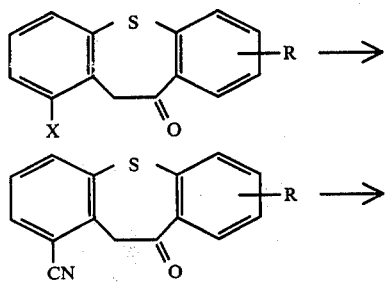

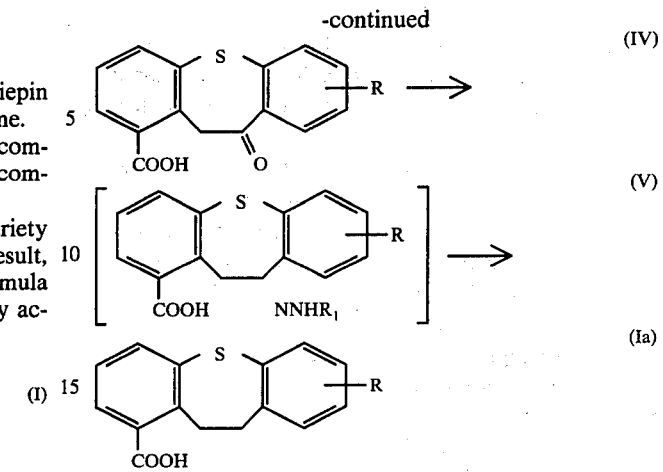

wherein R is as defined above, $R_1$ represents a hydrogen atom or the group of the formula —CONH$_2$ and X represents a bromine or chlorine atom.

According to the present process 1, 9-carboxy-10,11-dihydrodibenzo[b,f]thiepin derivatives of the formula (Ia) are produced by a process which comprises reacting 9-halogeno-10, 11-dihydro-11-oxo-dibenzo[b,f]thiepin derivatives of the formula (11) with cyanide compounds to produce 9-cyano-10,11-dihydro-11-oxo-dibenzo[b,f]thiepin derivatives of the formula (III), hydrolyzing the compounds (III) to produce 9-carboxy-10,11-dihydro-oxo-dibenzo[b,f]thiepin derivatives of the formula (IV), reacting the compounds (IV) with hydrazine or semicarbazide to produce hydrazone or semicarbazone of 9-carboxy-10,11-dihydro-11-oxo-dibenzo[b,f]thiepin derivatives of the formula (V) and then treating the compounds (V) with alkaline reagents.

Suitable cyanide compounds which may be used in the process for producing the compound of the formula (III) from the compound of the formula (II) include metallic cyanides, such as copper cyanide, potassium cyanide and sodium cyanide. The reaction is preferably conducted in N-methylpyrrolidone in view of its solubility, but any solvent which does not participate in the reaction may be used. After the completion of reaction, the compounds of the formula (III) may be isolated from the mixture by usual methods. For example, aqueous ammonia is added to the mixture, which is extracted with organic solvent and the solvent is evaporated to obtain the compounds of the formula (III).

Preferable catalysts to be used in the process for producing the compound of the formula (IV) from the compound of the formula (III) include mineral acids, such as hydrochloric acid and sulfuric acid, and alkaline reagents, such as sodium hydroxide, potassium hydroxide, metal alkoxide and barium hydroxide. The reaction is preferably conducted in hydrous organic solvents at an elevated temperature. After the completion of reaction, the compounds of the formula (IV) are isolated from the mixture by usual methods. For example, the reaction mixture is concentrated to obtain the residue, to which is added water and the resulting mixture is washed with ether. The aqueous layer is acidified with hydrochloric acid to separate the compounds of the formula (IV), which is collected by filtration. Or the acidic aqueous layer is extracted with organic solvent and the solvent is evaporated to obtain the compounds of the formula (IV).

In producing the compounds of the formula (V) from the compound of the formula (IV), the compounds of the formula (IV) may be reacted with hydrazine or semicarbazide in the solvent which does not participate in the reaction, for example, alcohols such as methanol and ethanol, and ethers such as dioxane and tetrahydrofuran.

In producing the compounds of the formula (Ia) from the compounds of the formula (V), the compounds (V) are reacted with alkaline agents in an inert solvent which does not participate in the reaction, for example, alcohols such as ethanol, t-butanol and diethyleneglycol, and ethers such as dioxane and tetrahydrofuran at an elevated temperature. Alkaline agents to be used in this reaction include potassium hydroxide, sodium hydroxide and metallic alkoxide.

During the course of this process, the group of the formula >C=NNHR$_1$ is reduced to the methylene group and at the same time R may be in part converted to a hydroxy group in the case where R stands for a lower alkoxy or fluorine atom, and when this process is conducted in diethyleneglycol, R may be in part converted to the group of the formula —OCH$_2$CH$_2$OCH$_2$CH$_2$OH in the case where R stands for fluorine atom. The compounds of the formula (Ia) can be obtained directly without the isolation of the compounds of the formula (V).

The compound of the formula (II), the starting material of this process 1, is produced by subjecting 6-halogeno-2-phenylthiophenylacetic acid or reactive derivatives thereof to ring closure reaction, as is shown by the following scheme:

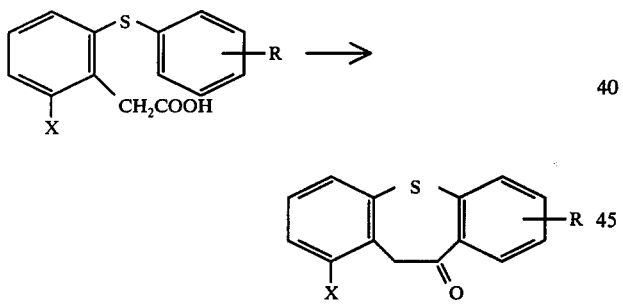

wherein R and X are as defined above.

The reactive derivatives to be used in the above process include acid halides, mixed acid anhydrides, and active esters. The reaction may be preferably conducted in the presence of polyphosphoric acid, polyphosphoric acid ethyl ester, conc. sulfuric acid, hydrogen fluoride, boron fluoride, aluminum chloride, titanium chloride, zinc chloride, tin chloride and trifluoroacetic acid.

Process 2:

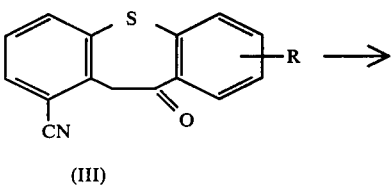

(III)

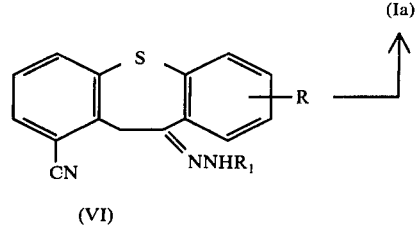

(VI)

wherein R and R$_1$ are as defined above.

According to the present process 2, 9-carboxy-10,11-dihydrodibenzo[b,f]thiepin derivatives of the formula (Ia) are produced by a process which comprises reacting 9-cyano-10,11-dihydro-11-oxo-dibenzo[b,f]thiepin derivatives of the formula (III) with hydrazine or semicarbazide to produce hydrazone or semicarbazone of 9-cyano-10, 11-dihydro-11-oxo-dibenzo[b,f]thiepin derivatives of the formula (VI) and treating the compounds of the formula (VI) with alkaline reagents.

The present process may be conducted under substantially same condition as in Process 1.

When the compound of the formula (VI) is reacted with alkaline agents, the group of the formula >C=NNHR$_1$ is reduced to a methylene group and at the same time a cyano group is hydrolyzed to a carboxyl group.

Process 3:

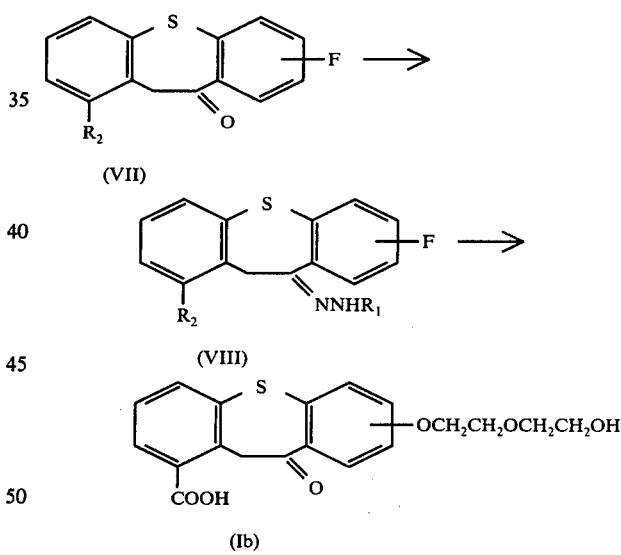

wherein R$_2$ represents a cyano or carboxyl group and R$_1$ is the same as defined above.

According to the present process 3, 9-carboxy-10,11-dihydrodibenzo[b,f]thiepin derivatives of the formula (Ib) are produced by a process which comprises reacting 9-substituted-10,11-dihydro-dibenzo[b,f]thiepin-11-one derivatives of the formula (VII) with hydrazine or semicarbazide to produce hydrazone or semicarbazone of 9-substituted-10,11-dihydrodibenzo[b,f]thiepin-11-one derivatives of the formula (VIII) and treating the compounds of the formula (VIII) with alkaline reagents in the presence of diethylene glycol.

A starting material of the formula (VII) may be easily prepared by reacting the compound of the formula (IX)

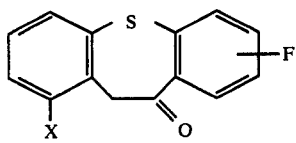

wherein X is as defined above, with metallic cyanides such as copper cyanide, potassium cyanide and sodium cyanide. 9-Carboxy derivatives are produced by hydrolyzing the 9-cyano derivatives obtained as described above.

In producing the compounds of the formula (VIII) from the compounds of the formula (VII) the compounds (VII) are reacted with hydrazine or semicarbazide in an inert organic solvent which does not participate in the reaction, for example, alcohols such as methanol and ethanol, and ethers such as dioxane and tetrahydrofuran. The reaction may be preferably conducted under reflux conditions for 3 to 8 hours.

In producing the compounds of the formula (Ib) from the compounds of the formula (VIII), the compounds of the formula (VIII) are reacted with alkaline agents such as potassium hydroxide, sodium hydroxide and metallic alkoxide in the presence of diethylene glycol at an elevated temperature. During the course of this reaction, the group of the formula $>C=NNHR_1$ is reduced to a methylene group and at the same time, a cyano group is hydrolyzed to a carboxy group, and a fluorine atom is converted to a diethylene glycoxy group, there is obtained the compound of the formula (Ib).

Process 4.

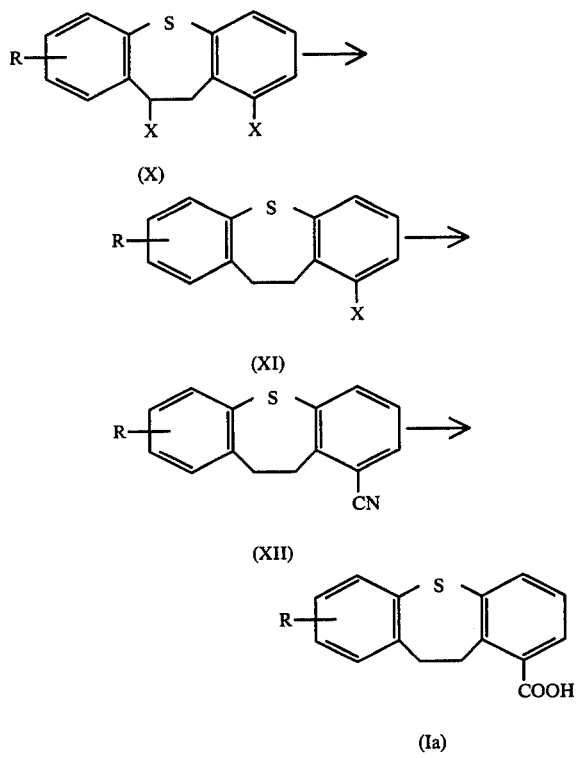

wherein R and X are as defined above.

According to the present process 9-carboxy-10,11-dihydrodibenzo[b,f]thiepin derivatives of the formula (Ia) are produced by the following process which comprises reducing 9-halogeno-11-halogeno-10, 11-dihydrodibenzo [b,f]thiepin derivatives of the formula (X) to produce 9-halogeno-10, 11-dihydrodibenzo [b,f]thiepin derivatives of the formula (XI), reacting the compounds of the formula (XI) with metallic cyanide compounds, thereby forming 9-cyano-10, 11-dihydrodibenzo[b,f]thiepin derivatives of the formula (XII) and hydrolyzing the compounds of the formula (XII).

In producing the compounds of the formula (XI) from the compounds of the formula (X), the compounds of the formula (X) are subjected to conventional reduction, with the use of reducing agents, such as lithiumaluminum hydride in an inert solvent which does not participate in the reaction and dissolves the compounds of the formula (X) such as tetrahydrofuran for several hours under reflux conditions.

In producing the compounds of the formula (XII) from the compounds of the formula (XI), the compounds of the formula (XI) are reacted with metallic cyanide compounds, such as copper cyanide, sodium cyanide, potassium cyanide and the like. Preferable solvents to be used in this reaction include N-methylpyrrolidone.

In producing the compounds of the formula (Ia) from the compounds of the formula (XII), usual methods are applicable. For example, the compounds of the formula (XII) are heated under reflux conditions in hydrous alcohol containing potassium hydroxide to obtain the compounds of the formula (Ia) in a good yield.

The starting material of the formula (X) is produced by reducing the compound of the formula (II), to obtain 9-halogeno-11-hydroxy-10, 11-dihydro-dibenzo[b,f]thiepin derivatives and halogenating the resulting compound, according to the following scheme.

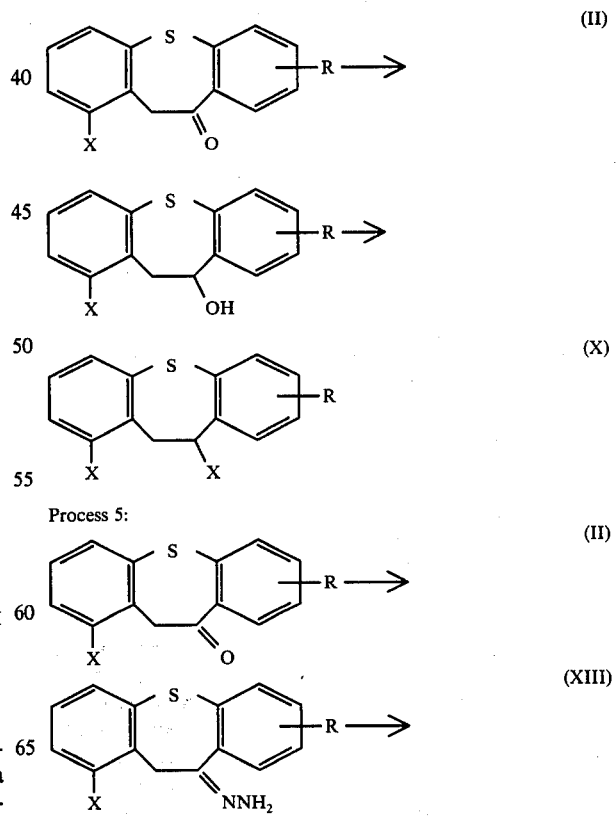

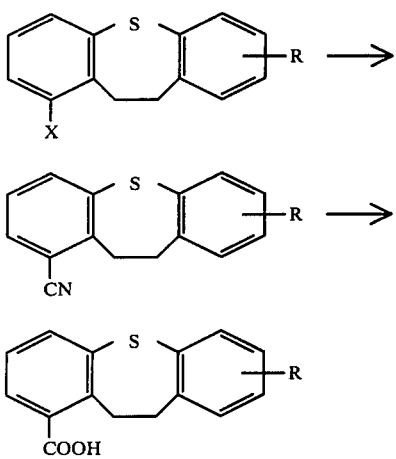

This process can be conducted in a similar manner to the above mentioned.

Process 6:

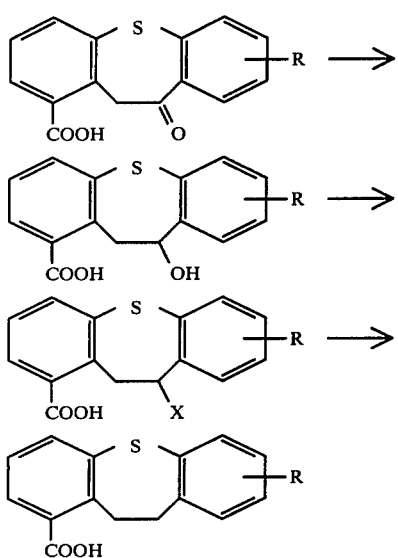

Reduction of a carbonyl group of the compound (IV) in Process 6 can be made by usual methods, preferably with the use of sodium boron hydride. In this case, the reaction proceeds effectively in organic solvents such as alcohols, for example, methanol and ethanol, and ethers, for example, dioxane and tetrahydrofuran at room temperature or an elevated temperature. After the completion of reaction, to the mixture water was added and the resulting mixture was extracted with organic solvent to obtain 9-carboxy-10, 11-dihydrodibenzo[b,f]-thiepin-11-ol derivatives of the formula (XIV).

9-Carboxy-10, 11-dihydro-11-halogenodibenzo[b,f]-thiepin derivatives of the formula (XV) are produced by reacting the compound of the formula (XIV) with a halogenating agent, such as phosphorus trichloride, phosphorus pentachloride, phosphorus oxychloride, thionyl chloride or oxalyl chloride with or without organic solvent which does not participate in the reaction, such as benzene, toluene, hexane and the like.

Reduction of the compound of the formula (XV) may be preferably in the presence of catalyst, such as platinum, palladium, nickel, cobalt, iron and copper. The use of lithium aluminum hydride, which may reduce a carboxy group, should be avoided in this reaction.

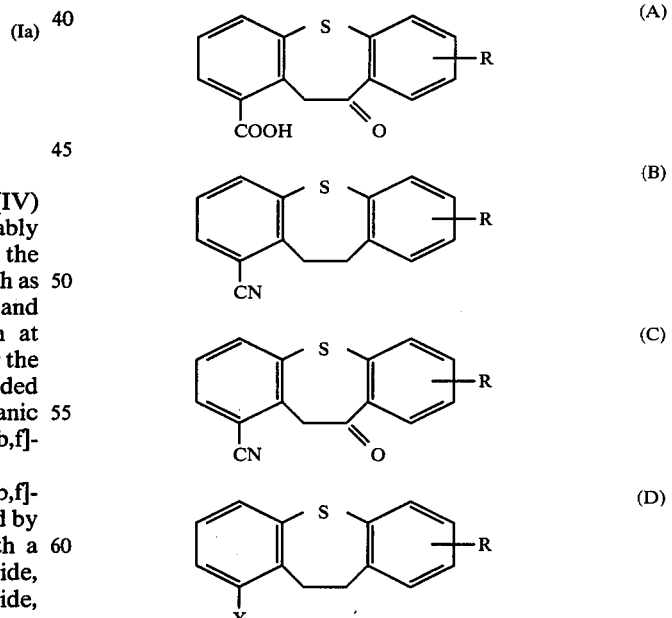

wherein R, $R_3$ and $R_4$ are as defined above.

According to the present process 7, 9-substituted-aminocarbonyl-10, 11-dihydrodibenzo[b,f]thiepin of the formula(Ic) is produced by reacting 9-carboxy-10, 11-dihydrodibenzo[b,f]-thiepin derivatives of the formula (Ia) produced by any one of the above processes, or reactive derivatives thereof, with amino compounds of the formula(XVI).

The active derivatives to be used in this process include acid halides, mixed acid anhydrides and active esters, and the usual methods for producing amides are applicable to this process.

Accordingly, particularly preferred intermediates of benzo [b,f]thiepin derivatives according to the present invention represented by the formula(I) are shown below, which are represented by the formulae (A)–(D).

wherein R and X are as defined above.

The compounds of the present invention represented by the formula (I) possess highly excellent antiinflammatory effects.

That is, Wister male rats were given orally the compounds according to the present invention and then induced edema on hind legs by carrageenan injection.

As a result, 30 to 60 percent inhibitory actions were observed at the 2nd hour after oral administration of the present compounds. Significant effects were found even after the 6th hour from the medication.

Wister male rats weighing 120 – 160 g were used, one group consisting of 5 to 7 rats.

Hind legs were given subcutaneous injections of 0.1 ml of 1% carrageenan at the 1st hour after the medication of 100 mg/kg of the test compounds, and volumes of hind legs were measured by volume differential meter.

The results obtained are shown in Table 1.

Table 1

| Test Compounds | Maximum Inhibitory Percentage (%) | Maximum Reaction Time (hr.) |
|---|---|---|
| Compound 1 | 38 | 3 |
| Compound 2 | 38 | 5 |
| Compound 3 | 50 | 5 |
| Compound 4 | 32 | 4 |
| Compound 5 | 38 | 4 |
| Compound 6 | 32 | 5 |
| Compound 7 | 41 | 2 |
| Compound 8 | 53 | 3 |
| Compound 9 | 35 | 2 |
| Compound 10 | 46 | 3 |

| Compound 1: | 2-methoxy-9-carboxy-10,11-dihydrodibenzo[b,f]thiepin |
|---|---|
| 2: | 2-methoxy-9-(diisopropylamino)carbonyl-10,11-dihydrodibenzo[b,f]thiepin |
| 3: | 2-diethyleneglycoxy-9-carboxy-10,11-dihydrodibenzo[b,f]thiepin |
| 4: | 3-diethyleneglycoxy-9-carboxy-10,11-dihydrodibenzo[b,f]thiepin |
| 5: | 3-fluoro-9-carboxy-10,11-dihydrodibenzo[b,f]thiepin |
| 6: | 2-fluoro-9-(diisopropylamino)carbonyl-10,11-dihydrodibenzo[b,f]thiepin |
| 7: | 2-trifluoromethyl-9-carboxy-10,11-dihydrodibenzo[b,f]thiepin |
| 8: | 2-trifluoromethyl-9-($\beta$-hydroxyethylpiperazinyl)-carbonyl-10,11-dihydrodibenzo[b,f]thiepin hydrochloride |
| 9: | 2-($\beta$-hydroxyethoxy)-9-carboxy-10,11-dihydrodibenzo[b,f]thiepin |
| 10: | 2-($\beta$-aminoethoxy)-9-carboxy-10,11-dihydrodibenzo[b,f]thiepin |

The compound 3,9-carboxy-2-diethyleneglycoxy-10,11-dihydrodibenzo[b,f]thiepin which exerts the most significant effect at the 5th hour after medication as shown in Table 1 was examined for the toxicity thereof in comparison with those of the existing medicaments.

Compound 3, phenylbutazone, flufenamic acid and mefenamic acid were dissolved in 1N-NaOH solution and the resulting solution was adjusted to pH 8 – 9 with 1N-HCl solution.

100 to 200 mg/kg of each compound was injected intravenously, using dd male mice weighing 20 – 30 g.

Counting of the number of deaths was performed at the 72nd hour after the administration.

The results obtained are shown in Table 2.

Table 2

| Compounds | The number of deaths | |
|---|---|---|
|  | 100 mg/kg | 200 mg/kg |
| Compound 1 | 0/5[a] | 0/5 |
| Phenylbutazone | 0/5 | 5/5 |
| Flufenamic acid | 1/5 | 5/5 |
| Mefenamic acid | 1/5 | 5/5 |

[a]the number of deaths/total number of animals

The invention is illustrated below in further detail with reference to Examples, but the invention is not limited to the Examples.

EXAMPLE 1

2-fluoro-9-chloro-10,11-dihydrodibenzo[b,f]thiepin-11-one:

To 0.1g of 2-chloro-6-(p-fluorophenylthio)phenylacetic acid was added 10g of polyphosphoric acid and the resulting mixture was stirred at 150° C for 2 hours. After cooling, to the mixture was added water and the mixture was extracted with benzene. The extract was washed with water, dried over anhydrous sodium sulfate and freed of solvent under reduced pressure. The residue obtained was recrystallized from benzene-n-hexane to afford 0.55g (58.8%) of 2-fluoro-9-chloro-10,11-dihydrodibenzo[b,f]thiepin-11-one as colorless crystals having a melting point of 135°–137° C.

Ir $\gamma_{max}^{KBr}$ cm$^{-1}$): 1660 (C=O)

EXAMPLE 2

2-fluoro-9-chloro-10,11-dihydrodibenzo[b,f]thiepin-11-one:

To 5.9g of 2-chloro-6-(p-fluorophenylthio)phenylacetic acid was added 60g of polyphosphoric acid and the resulting mixture was stirred at 150° C for 2 hours. After cooling, to the mixture was added ice and the thus obtained precipitate was extracted with benzene-diethyl ether. The extract was dried over anhydrous sodium sulfate and freed of solvent by distillation. The residue was washed with diethyl ether-n-hexane, there was obtained 3.5g (55%) of 2-fluoro-9-chloro-10,11-dihydrodibenzo[b,f]thiepin-11-one as colorless crystals. A part of this product was recrystallized from benzene-n-hexane (3/1) to afford colorless granules having a melting point of 136°–137° C.

| Elemental Analysis : as $C_{14}H_8OSClF$ | |
|---|---|
| Calculated (%) : | C: 60.33 H: 2.89 |
| Found (%) : | C: 60.61 H: 2.86 |
| IR ($\gamma_{max}^{CHCl_3}$ cm$^{-1}$) : | 1670 (C=O) |
| NMR (CDCl$_3$) $\delta$ : | 4.62 (2H, S, $C_{10}-H_2$) |
| | 7.00–8.00 (6H, m, aromatic protons) |

EXAMPLE 3

9-cyano-2-fluoro-10,11-dihydro-11-oxo-dibenzo[b,f]thiepin:

The mixture of 3.4g of 9-chloro-2-fluoro-10,11-dihydro-11-oxo-dibenzo[b,f]thiepin, 2.1g of copper cyanide, 0.2g of anhydrous copper sulfate and 50ml of N-methyl pyrrolidone was heated at 200°–210° C overnight. After cooling, to the reaction mixture were added 10ml of conc. aqueous ammonia and 100ml of water and the resulting mixture was extracted with benzene. The benzene layer thus obtained was washed with water, dried over anhydrous sodium sulfate and the solvent was distilled off. The resulting residue was chromatographed over silica gel, and eluted with chloroform and benzene. There was obtained from benzene eluate 0.3g of 9-cyano-2-fluoro-10,11-dihydro-11-oxo-dibenzo[b,f]thiepin as yellow needles having a melting point of 174°–175° C.

| Elemental Analysis : as $C_{15}H_8ONSF$ | |
|---|---|
| Calculated (%) : | C: 66.90 H: 2.99 N: 5.20 |
| Found (%) : | C: 66.68 H: 2.87 N: 4.94 |
| IR $(\gamma_{max}^{CHCl_3}$ cm$^{-1})$ : | 2218 (CN), 1680 (C=O) |
| NMR (CDCl$_3$) : | 4.63 (2H, singlet, CH$_2$) |
| MS (m/e) : | 269 (M$^+$) |

EXAMPLE 4

9-carboxy-2-fluoro-10,11-dihydro-11-oxo-dibenzo[b,f]thiepin:

The mixture of 0.5g of 9-cyano-2-fluoro-10,11-dihydro-11-oxo-dibenzo[b,f]thiepin, 0.8g of potassium hydroxide and 5ml of 90% ethanol was heated overnight under reflux. After the completion of reaction, the reaction mixture was concentrated under reduced pressure and 50ml of water was added to dissolve the residue which was extracted with diethyl ether. The aqueous layer was acidified with conc. hydrochloric acid to give crystals which were extracted diethyl ether.

The extract was washed with saturated saline solution and dried over anhydrous sodium sulfate. The solvent was distilled off to obtain the residue which was recrystallized from benzene-hexane, and there was obtained 0.5g of 9-carboxy-2-fluoro-10,11-dihydro-11-oxo-dibenzo[b,f]thiepin as pale yellow granules having a melting point of 242°–244° C.

EXAMPLE 5

9-cyano-2-fluoro-10,11-dihydrodibenzo[b,f]thiepin-11-one hydrazone:

The mixture of 0.3g of 9-cyano-2-fluoro-10,11-dihydrodibenzo[b,f]thiepin-11-one, 0.3g of 100% hydrazine hydrate and 10ml of ethanol was heated under reflux on water-bath for 5 hours. The reaction mixture was concentrated to 5ml to separate crystals on cooling, which was collected by filtration. Recrystallization from ethanol afforded 0.3g of 9-cyano-2-fluoro-10,11-dihydrodibenzo[b,f]thiepin-11-one hydrazone as pale yellow needles having a melting point of 220°–222° C.

| Elemental Analysis : as $C_{15}H_{10}N_3SF$ | |
|---|---|
| Calculated (%) : | C: 63.59 H: 3.56 N: 14.83 |
| Found (%) : | C: 63.46 H: 3.47 N: 15.23 |
| IR $(\gamma_{max}^{KBr}$ cm$^{-1})$ : | 3410 (NH$_2$), 2240 (CN) |
| MS (m/e) : | 283 (M$^+$) |

EXAMPLE 6

9-carboxy-2-diethyleneglycoxy-10,11-dihydrodibenzo[b,f]thiepin:

The mixture of 0.3g of 9-cyano-2-fluoro-10,11-dihydrodibenzo[b,f]thiepin-11-one hydrazone, 0.3g of sodium hydroxide and 6ml of diethylene glycol was heated with stirring at 190°–200° C. After cooling, 100ml of water was added to the reaction mixture, which was extracted with diethyl ether. The aqueous layer was acidified with water to separate crystals, which was extracted with ethyl acetate. The extract was washed with saturated saline solution and dried over anhydrous sodium sulfate. The solvent was evaporated under reduced pressure to obtain the residue, which was chromatographed over silica gel, and eluted with benzene-ethyl acetate (1:1). Recrystallization of the crude product from diethyl ether-petroleum ether afforded 100mg of 9-carboxy-2-diethyleneglycoxy-10,11-dihydrodibenzo[b,f]thiepin having a melting point of 114°–116° C.

| Elemental Analysis : as $C_{19}H_{20}O_5S$ | |
|---|---|
| Calculated (%) : | C: 63.33 H: 5.59 |
| Found (%) : | C: 63.32 H: 5.66 |
| IR $(\gamma_{max}^{KBr}$ cm$^{-1})$ : | 1680 (C=O) |
| NMR (CD$_3$OD) δ : | 3.22–4.10 (13H, m, methylene protons due to diethylene glycol ether and C$_{10}$, C$_{11}$ protons) |
| MS (m/e): | 360 (M$^+$) |

EXAMPLE 7

2-fluoro-9-(N,N-diisopropyl)aminocarbonyl-10,11-dihydrodibenzo[b,f]thiepin:

An amount of 487.5mg of 2-fluoro-9-carboxy-10,11-dihydrodibenzo[b,f]thiepin was dissolved in 20ml of anhydrous benzene and to the resulting mixture was added dropwise 2ml of thionyl chloride. After dropping, the mixture was refluxed for about 5 hours and freed of solvent under reduced pressure. The thus obtained residue was dissolved in 20ml of anhydrous benzene and to the mixture was added 2.5ml of diisopropyl amine. The mixture was refluxed for about 3hours and freed of solvent under reduced pressure. To this was added water and the mixture was extracted with benzene. The extract was washed with water, dried over anhydrous sodium sulfate and freed of solvent under reduced pressure to obtain 190mg of pale yellow residue. This was recrystallized from n-hexane to give 144mg (22%) of 2-fluoro-9-(N,N-diisopropyl)aminocarbonyl-10,11-dihydrodibenzo[b,f]thiepin as colorless crystals having a melting point of 149°–150.5° C IR $(\gamma_{max}^{KBr}$ cm$^{-1})$: 1620 (C=O)

MS (m/e): 357 M$^+$)

EXAMPLE 8

9-cyano-2-methoxy-10,11-dihydro-11-oxo-dibenzo[b,f]thiepin:

To 50ml of N-methylpyrrolidone were added 5.8g of 9-fluoro-methoxy-10,11-dihydro-11-oxo-dibenzo[b,f]thiepin, 5.4g of copper cyanide and 0.2g anhydrous copper sulfate, and the resulting mixture was heated with stirring at 230°–240° C for 14 hours. After cooling, to the reaction mixture were added 200ml of 28% aqueous ammonia and 320ml of water, and the resulting mixture was extracted with benzene. The aqueous and benzene layers were filtered through celite. The collected benzene layer was washed with water several times, diluted hydrochloric acid and then water, which was dried over anhydrous sodium sulfate. The solvent was evaporated to obtain about 6g of residue which was chromatographed on silica gel. 1.0g of the starting material was recovered from benzene/chloroform (1/1 ) eluate and there was obtained from chloroform eluate 9-cyano-2-methoxy-10,11-dihydro-11-oxo-dibenzo[b,f]thiepin, which was washed with ethanol to give 2.1g of pale yellow needles having a melting point of 188°–189° C.

IR (KBr, cm$^{-1}$): 2240 (CN), 1675 (CO)

NMR (CDCl$_3$, ppm): 3.80 (3H, S, —OCH$_3$), 4.65 (2H, S, —CH$_2$), 6.88–7.92 (6H, m, aromatic protons) MS (m/e): 281 (M$^+$)

EXAMPLE 9

9-carboxy-2-methoxy-10,11-dihydrodibenzo[b,f]thiepin-11-one:

To the mixture of 1ml of water and 600mg of potassium hydroxide in 9ml of ethanol was added 200mg of 9-cyano-2-methoxy-10,11-dihydro-11-oxo-dibenzo[b,f]thiepin and the resulting mixture was heated under reflux overnight. Water was added to the mixture, which was washed with benzene. Aqueous layer was acidified with hydrochloric acid, extracted with chloroform, washed with water and dried over anhydrous sodium sulfate. The solvent was evaporated therefrom and there was obtained 130mg of 9-carboxy-2-methoxy-10,11-dihydro-11-oxo-dibenzo[b,f]thiepin having a melting point of 157°–160° C.

IR ($\gamma_{max}^{KBr}$ cm$^{-1}$): 1680 (CO) MX (m/e): 300 (M$^+$)

EXAMPLE 10

9-carboxy-2-methoxy-10,11-dihydrodibenzo[b,f]thiepin and 9-carboxy-2-hydroxy-10,11-dihydrodibenzo[b,f]thiepin:

To the mixed solvent of 16ml of ethanol and 16ml of dioxane were added 1.8g of 9-carboxy-2-methoxy-10,11-dihydro-11-oxo-dibenzo[b,f]thiepin and 2.0g of hydrazine hydrate and the resulting mixture was heated under reflux for 8 hours. After the completion of reaction, the solvent was distilled off and 1.8g of sodium hydroxide and 30ml of diethylene glycol was added to the residue. The thus obtained mixture was heated under reflux at 190°–200° C for 5 hours. After cooling, water was added to the mixture which was extracted benzene. The aqueous layer was acidified with hydrochloric acid and extracted with benzene. The extract was washed with water, dried and the solvent was distilled off. The thus obtained residue was chromatographed over silica gel, eluted with chloroform-diethylether (10:1), there was obtained 0.5G of 9-carboxy-2-methoxy-10,11-dihydrodibenzo[b,f]thiepin as colorless needles having a melting point of 185°–187° C.

| Elemental analysis : as C$_{16}$H$_{14}$O$_3$S | |
|---|---|
| Calculated (%) : | C: 67.11 H: 4.93 |
| Found (%) : | C: 67.36 H: 5.05 |

As eluted with diethyl ether, there was obtained 0.3g of 9-carboxy-2-hydroxy-10,11-dihydrodibenzo[b,f]thiepin as pale yellow prismatic crystals having a melting point of 210°14 211° C.

IR ($\gamma_{max}^{KBr}$): 3600–3000 (COOH, OH), 1710–1690 (CO)

| Elemental Analysis : as C$_{15}$H$_{12}$O$_3$S | |
|---|---|
| Calculated (%) : | C: 66.16 H: 4.44 |
| Found (%) : | C: 65.95 H: 4.27 |

EXAMPLE 11

2-methoxy-9-(N,N-diisopropyl)aminocarbonyl-10,11-dihydrodibenzo[b,f]thiepin:

An amount of 572mg of 2-methoxy-9-carboxy-10,11-dihydrodibenzo[b,f]thiepin was dissolved in 10ml of anhydrous benzene and to the mixture was added 1ml of thionyl chloride. The resulting mixture was refluxed for 3 hours and freed of solent under reduced pressure to obtain 614mg of 2-methoxy-10,11-dihydrodibenzo[b,f]thiepin-9-carbonyl chloride.

IR $\gamma$KBr/max cm$^{-1}$): 1765 (COCl)

The above chloride was dissolved in 10ml of anydrous benzene and to the solution was added 1.0g of diisopropyl amine. The resulting mixture was refluxed for 6 hours. After cooling, to the mixture was added ethyl acetate and the mixture was washed with saturated sodium chloride solution, dried over anhydrous sodium sulfate and freed of solvent under reduced pressure to obtain 660mg of pale brown crystals.

This was chromatographed over silica gel, and eluted with chloroform-methanol (10/1), there was obtained 647mg (87%) of pale brown crystals. This was recrystallized from benzen-n-hexane to afford 317mg of 2-methoxy-9-(N,N-diisopropyl)-aminocarbonyl-10,11-dihydrodibenzo[b,f]thiepine as colourless prismatic crystals having a melting point of 139°–140° C.

IR $\gamma$KBr/max cm$-1$): 1635 (CON>)

NMR (CDCl$_3$) : 1.0–1.6 (6H, m, CH$_3\times$2), 1.59–1.64 (6H, m, CH$_3\times$2), 3.1–3.8 (4H, m. —CH$_2$CH$_2$–), 3.74 (2H, s, OCH$_3$), 6.56–6172 (2H, m, aromatic protons), 6.92–7.53 (4H, m, aromatic protons)

MS (m/e): 369 (M$^+$)

EXAMPLE 12

9-cyano-2-methoxy-10,11-dihydrodiebenzo[b,f]thiepin-11-hydrazone:

900mg of 9-cyano-2-methoxy-10,11-dihydro-11-oxo-dibenzo-[b,f]thiepin was dissolved in the mixed solvent of 8ml of ethanol and 8ml of dioxane. To this was added 1.0g of 100% hydrazine hydrate and the resulting mixture was refluxed with stirring for 7.5 hours. After the completion of reaction, the solvent was distilled off to obtain the residue, which was washed with a small amount of ethanol, and there was obtained 750mg of 9-cyano-2-methoxy-10,11-dihydro-11-oxo-dibenzo[b,f]thiepin hydrazone as colorless needles having a melting point of 186°–187° C.

IR (KBr, cm$^{-1}$): 3360 (NH), 3280 (NH), 2230 (CN)

NMR (CDCl$_3$-DMSO, ppm) : 3.20 (1H, broad, NH), 3.65 (3H, s, -OCH$_3$), 4.32 (2H, S, —CH$_2$—), 6.24 (1H, broad, —NH), 6.72 (1H, q, J=10 cps, J=2 cps, aromatic protons) 7.16–7.92 (5H, m, aromatic protons)

MS (m/e : 295 (M$^+$)

EXAMPLE 13

9-carboxy-2-methoxy-10,11-dihydrodibenzo[b,f]thiepin:

600mg of 9-cyano-2-methoxy-10,11-dihydro-11-oxo-dibenzo-[b,f]thiepin hydrazone and 600mg of sodium hydroxide were added to 10ml of diethylene glycol and the resulting mixture was heated with stirring at 190°–200° C for 5 hours. After cooling, water was added to the mixture, which was extracted with benzene. The aqueous layer was acidified with hydrochloric acid and extracted with benzene. The benzene extract was washed with water and dried over anhydrous sodium sulfate. The solvent was evaporated to obtain the residue, which was chromatographed over silica gel and eluted with chloroform-ether (10:1). There was obtained 9-carboxy-2-methoxy-10,11-dihydrodibenzo[b,f]thiepin. Recrystallization from benzene afforded 140mg of the desired product as colorless needles having a melting point of 185°–187° C.

IR (KBr, cm⁻): 3200–2600 (COOH), 1685 (CO)

NMR (DMSO, ppm): 3.04–3.36 (2H, broad, —CH$_2$—) 3.36–3.72 (5H, broad, —CH$_2$— and —OCH$_3$—) 6.44–6.70 (2H, m), 6.80–7.60 (5H, m, aromatic protons and —COOH)

MS (m/e) : 286 (M$^+$)

As eluted with ether, there was obtained 9-carboxy-2-hydroxy-10,11-dihydrodibenzo[b,f]thiepin. Recrystallization from benzene afforded 100mg of the desired product as pale yellow prismatic cyrstals having a melting point of 210–211° C.

IR (KBr, cm⁻¹): 3600–3000 (COOH and OH), 1710–1680 (CO)

NMR (DMSO, ppm) : 3.80–3.44 (2H, broad, —CH$_2$—), 3.44–3.89 (2H, broad, —CH$_2$—), 6.40–6.70 (2H, m), 7.00–7.80 (4H, m)

MS (m/e) : 272 (M$^+$)

EXAMPLE 14

2-hydroxy-9-ethoxycarbonyl-10,11-dihydrodibenzo[b,f]thiepin:

An amount of 1.7g of 2-hydroxy-9-carboxy-10,11-dihydrodibenzo[b,f]thiepin was dissolved in 50ml of anhydrous ethanol and the mixture was refluxed for 3 hours, while hydrogen chloride gas was bubbled into the mixture. The solvent was distilled off to obtain the residue which was dissolved in the mixed solvent of ethyl acetate-benzene. The solution was washed with saturated sodium chloride solution and freed of solvent by distillation to obtain 1.6g (85%) of 2-hydroxy-9-ethoxycarbonyl-10,11-dihydrodibenzo[b,f]thiepin as brown crystals having a melting point of 125°–129° C.

EXAMPLE 15

2-($\beta$-phthalylamino)ethoxy-9-ethoxycarbonyl-10,11-dihydrodibenzo[b,f]thiepin:

The mixture of 780mg of 2-hydroxy-9-ethoxycarbonyl-10,11-dihydrodibenzo[b,f]thiepin, 1320mg of $\beta$-phenthalylaminoethyl bromide and 250mg of sodium hydride was gradually heated with stirring and then refluxed at 180°–190° C. for 4 hours. After cooling, the mixture was dissolved in the mixed solvent of ethyl acetate and methanol, washed with saturated sodium chloride solution, dried over anydrous sodium sulfate and freed of solvent under reduced pressure. The resulting residue was chromatographed over a silica gel, and eluted with chloroform, there was obtained the product. This was recrystallized from benzene-n-hexane to afford 580mg (47%) of 2-($\beta$-phthalylamino) ethoxy-9-ethoxycarbonyl-10,11-dihydrodibenzo[b,f]thiepin as colorless crystals.

EXAMPLE 16

2-($\beta$-amino)ethoxy-9-ethoxycarbonyl-10,11-dihydrodibenzo[b,f]thiepin:

An amount of 330mg of 2-($\beta$-phthalylamino) ethoxy-9-ethoxycarbonyl-10,11-dihydrodibenzo[b,f]thiepin was dissolved in ethanol and to the resulting solution was added 1ml of hydrazine hydrate and the mixture was refluxed for 1 hour. After cooling, the separated substance was filtered off and the filtrate was freed of solvent. The residue was dissolved in ethanol and cooled. The separated substance was filtered off and the filtrate was freed of solvent to obtain the residue, which was dissolved in chloroform and cooled. This solution was filtered and the filtrate was evaporated to obtain 217mg (92%) of 2-($\beta$-amino) ethoxy-9-ethoxycarbonyl-10,11-dihydrodibenzo[b,f]thiepin as pale yellow crystals.

EXAMPLE 17

2-($\beta$-amino)ethoxy-9-carboxy-10,11-dihydrodibenzo[b,f]thiepin:

An amount of 309mg of 2-($\beta$-amino)ethoxy-9-ethoxycarbonyl-10,11-dihydrodibenzo[b,f]thiepin was dissolved in 15ml of ethanol and to the solution was added 10ml of 5N sodium hydroxide solution. The mixture was stirred at room temperature for 2 hours and freed of solvent under reduced pressure to obtain the residue, which was dissolved in water and washed with ethyl acetate. The aqueous layer was acidified with conc. hydrochloric acid and extracted with ethyl acetate-methanol. The extract was washed with saturated sodium chloride solution, dried over anhydrous sodium sulfate and freed of solvent to obtain 90mg of powder. The aqueous layer was freed of water under reduced pressure at 50° C to obtain the residue, which was extracted with ethanol. The extract was freed of ethanol under reduced pressure to obtain the residue, which was dissolved in ethanol. This solution was filtered, using elite and the filtrate was freed of solvent to obtain 225mg of powder.

Both powders were combined, dissolved in hydrous ethanol and adsorbed by 20ml of Dow Ex-1 (X-4, OH form), which was fully washed with hydrous ethanol. When eluted with 2N-HCl-ethanol (1/1), there was obtained white powder. This was recrystallized from anhydrous ethanol-diethyl ether to afford 81mg (26%) of 2-($\beta$-amino)ethoxy-9-carboxy-10,11-dihydrodibenzo[b,f]thiepin as white powder having a melting point of 220°–223° C.

IR $\beta$KBr/max cm⁻¹) : 1695 (C=O)

MS (m/e) : 315 (M$^+$—HCl)

EXAMPLE 18

2-($\beta$-tetrahydropyranyloxy)ethoxy-9-carboxy-10,11-dihydrodibenzo[b,f]thiepin:

To 6ml of hexamethylphosphorylamide was added 164mg of 2-hydroxy-9-ethoxycarbonyl-10,11-dihydrodibenzo[b,f]thiepin and 82mg of sodium hydride and the resulting mixture was stirred at room temperature for 2 hours. To the mixture was added 250mg of 2-($\beta$-bromoethoxy) tetrahydropyran and the mixture was stirred at 130° C for 19 hours. After cooling, to the mixture was added water and the mixture was extracted with ethyl acetate.

The aqueous layer was acidified with hydrochloric acid, extracted ethyl acetate, and the extract was washed with water, dried over anhydrous sodium sulfate and freed of the solvent under reduced pressure to obtain 200mg of brown oil. This was chromatographed over, silica gel, and eluted with benzene-ethanol (100/1), and there was obtained 112mg of pale brown oil.

This was recrystallized from benzene-n-hexane to afford 97mg (44.5%) of 2-($\beta$ -tetrahydropyranyloxy)ethoxy-9-carboxy-10,11-dihydrodibenzo [b,f]thiepin as colorless crystals having a melting point of 127°–128.5° C.

NMR (CDCl$_3$)$\delta$ : 1.40–1.96 (6H, m, methylene protons), 3.24–4.14 (10H, m, methylene protons), 4.60–4.84 (1H, m, methylene proton), 6.60–8102 (6H, m, aromatic protons)

MS (m/e): 400 (M$^+$)

EXAMPLE 19

2- (β-hydroxy)ethoxy-9-carboxy-10,11-dihydrodibenzo[b,f]-thiepin:

To the mixed solvent of 6ml of conc. hydrochloric acid and 6ml of water was added 100mg of 2-(β-tetrahydropyranyloxy)ethoxy-9-carboxy-10,11-dihydrodibenzo[b,f]thiepin and the mixture was stirred at room temperature for 2 hours, made basic with diluted sodium hydroxide solution and washed with benzene. The aqueous layer was acidified with hydrochloric acid and extracted with ethyl acetate. The extract was washed with water, dried over anhydrous sodium sulfate and freed of the solvent under reduced pressure to obtain a pale yellow residue. This was recrystallized from benzene to afford 68mg of 2-(β-hydroxy)ethoxy-9-carboxy-10,11-dihydrodibenzo[b,f]thiepin as colorless crystals having a melting point of 166°–168° C.

IR (γKBr/max cm$^{-1}$): 1680 (C=O)

NMR [(CD$_3$)$_2$CO]δ : 3.20–3.56 (2H, m, methylene protons), 3.60–4.20 (6H, m, methylene protons), 6.56–8.00 (6H, m, aromatic protons)

MS (m/e): 316 (M$^+$), 272 (M$^+$-44)

EXAMPLE 20

9-chloro-10,11-dihydrodibenzo[b,f]thiepin-11-one:

The mixture of 22g of 2-chloro-6-phenylthiophenylacetic acid and 220g of polyphosphoric acid was stirred at 120°–130° C for 2 hours. After cooling, to the mixture was added ice-water and the mixture was extracted with chloroform. The extract was washed with water, saturated sodium bicarbonate solution, then water, and dried over anhydrous sodium sulfate. The solvent was distilled off to obtain a residue, which was recrystallized from diethyl ether to afford 14.5g (66%) of 9-chloro-10,11-dihydrodibenzo[b,f]thiepin-11-one as colorless nedles having a melting point of 122°–125° C.

| Elemental Analysis : as C$_{14}$H$_{19}$OSCl | |
|---|---|
| Calculated (%) : | C: 64.49 H: 3.48 |
| Found (%) : | C: 64.66 H: 3.31 |
| IR (γ$_{max}$$^{CHCl_3}$ cm$^{-1}$) : | 1680 (C=O) |
| NMR (CDCl$_3$) δ : | 4.62 (2H, s, C$_{10}$—H$_2$), |
| | 7.00–7.63 (6H, m, aromatic protons), |
| | 8.23 (1H, d, J=7.6Hz, J=3.3Hz, C$_1$—H) |
| MS (m/e) : | 262, 260 (M$^+$) |

EXAMPLE 21

9-cyano-10,11-oxo-dibenzo[b,f]thiepin:

The mixture of 2.6g of 9-chloro-10,11-dihydro-11-oxo-dibenzo-[b,f]thiepin, 2.0g of copper cyanide, 0.1g of anhydrous copper sulfate and 50ml of N-methyl pyrrolidone was heated with stirring at 200° C overnight in a flask equipped with a tube packed with silica gel. After cooling, to the reaction mixture were added 100ml of conc. aqueous ammonia and 200ml of water, and the resulting mixture was extracted with benzene. The extract was washed with water, diluted hydrochloric acid and then water, which was dried over potassium sulfate and the solvent evaporated therefrom. The residue thus obtained was chromatographed on 200g of silica gel, and eluted with chloroform/methanol (50/1). 0.6g of the starting material was recovered from a first eluate. Recrystallization of the residue of a second eluate from benzene gave 0.7g of 9-cyano 10,11-dihydro-11-oxo-dibenzo[b,f]thiepin as pale yellow prismatic crystals having a melting point of 165°–167° C.

| Elemental Analysis : as C$_{15}$H$_9$ONS | |
|---|---|
| Calculated (%) : | C: 71.58 H: 3.60 N: 5.57 |
| Found (%) : | C: 71.68 H: 3.34 N: 5.35 |
| IR (γ$_{max}$$^{CHCl_3}$ cm$^{-1}$) : | 2220 (CN), 1680 (CO) |
| NMR (CDCl$_3$) δ : | 4.64 (2H, singlet, C$_{10}$—H$_2$) |
| | 7.15–7.82 (7H, multiplet, aromatic protons) |
| MS (m/e) : | 251 (M$^+$) |

EXAMPLE 22

9-carboxy-10,11-dihydro-11-oxo-dibenzo[b,f]thiepin:

3.5g of 9-cyano-10,11-dihydro-11-oxo-dibenzo[b,f]thiepon was dissolved in 30ml of 33% potassium hydroxide solution (80% ethanol) and the resulting mixture was heated overnight under reflux. After the mixture was concentrated, water was added to dissolve the residue which was extracted with diethyl ether. The aqueous layer was acidified with conc. hydrochloric acid, extracted with mixed solvent of diethyl ether-ethyl acetate (1:1), washed with saturated saline solution and dried over anhydrous sodium sulfate. The solvent was evaporated and there was obtained 3.4g of 9-carboxy-10,11-dihydro-11-oxo-dibenzo[b,f]thiepin as pale yellow needles having a melting point of 230°–232° C.

IR (γKBr/max cm$^{-1}$): 1730 (COOH), 1650 (CO)

MS (m/e): 270 (M$^+$)

EXAMPLE 23

9-carboxy-10,11-dihydrodibenzo[b,f]thiepin:

The mixture of 1.0g of 9-carboxy-10,11-dihydro-11-oxodibenzo[b,f]thiepin, 1.0g of hydrazine hydrate and 30ml of ethanol was heated under reflux on water bath for 4 hours. The reaction mixture was concentrated to about 15ml to separate crystals on cooling, which were collected by filtration. They were added to the mixture of 1.0g of sodium hydroxide and 20ml of diethylene glycal and the resulting mixture was heated with stirring at 190°–200° C for 2 hours. After cooling, 300ml of water was added to the mixture, which was extracted with diethyl ether. The aqueous layer was acidified with conc. hydrochloric acid and extracted with chloroform and the solvent was evaporated therefrom. The thus obtained residue was chromatographed over silica gel and eluted with benzene-ethyl acetate (1:1), and there was obtained 0.4g of 9-carboxy-10,11-dihydrodibenzo[b,f]thiepin as yellow prismatic crystals having a melting point of 186°–187° C.

Elemental Analysis: As C$_{15}$H$_{12}$O$_2$S
Calculated (%): C: 70.28 H: 4.72
Found: (%): C: 70.40 H: 4.81

EXAMPLE 24

9-cyano-10,11-dihydrodibenzo[b,f]thiepin-11-hydrazone:

0.9g of 9-cyano-10,11-dihydro-11-oxo-dibenzo[b,f]thiepin and 1g of 100% hydrazine hydrate were dissolved in 10ml of ethanol and the resulting mixture was heated under reflux for 3.5 hours. The reaction mixutre was concentrated to 5ml to separate crystals on cooling, which were collected by filtration. Recrystallization from ethanol afforded 0.6g of 9-cyano-10,11-dihydro-11-oxo-dibenzo-[b,f]thiepin hydrazone as pale brown prismatic crystals having a melting point of 175°–177° C.

IR (γKBr/max cm$^{-1}$): 3390 (NH$_2$), 2205 (CN)

NMR [CDCl$_3$+(CD$_3$)$_2$SO]δ: 4.38 (2H, singlet, C$_{10}$—H$_2$) 7.18-7.98 (7H, multiplet, aromatic protons)
MS (m/e): 265 (M$^+$)

EXAMPLE 25

9-carboxy-10,11-dihydrodibenzo[b,f]thiepin:

The mixture of 0.5g of 9-cyano-10,11dihydro-11-oxo-dibenzo-[b,f]thiepin hydrazone. 0.5g of sodium hydroxide and 10ml of diethylene glycol was heated with stirring at 190°-200° C for 5 hours. After cooling, 50ml of water was added to the mixture, which was extracted with 50ml of diethyl ether. The aqueous layer was acidified with conc. hydrochloric acid to separate crystals, which were extracted with benzene.

The benzene extract was washed with saturated saline solution, and dried over anhydrous sodium sulfate. The solvent was evaporated under reduced pressure. The thus obtained residue was recrystallized from benzene, and there was obtained 0.4g of 9-carboxy-10,11-dihydrodibenzo[b,f]thiepin as yellow prismatic crystals having a melting point of 187°-188° C.

| Elemental Analysis : as C$_{15}$H$_{12}$O$_2$S | |
| --- | --- |
| Calculated (%) : | C: 70.28 H: 4.72 |
| Found (%) : | C: 70.37 H: 4.58 |
| IR ($\gamma_{max}^{KBr}$ cm$^{-1}$) : | 1685 (CO) |
| NMR[CDCl$_3$ + (CD$_3$)$_2$SO]δ : | 3.26-3.40 (2H, multiplet, C$_{11}$—H$_2$), |
| | 3.78-3.89 (2H, multiplet, C$_{10}$—H$_2$), |
| | 7.08-7.83 (2H, multiplet, aromatic protons) |
| MS (m/e) : | 256 (M$^+$) |

EXAMPLE 26

4-fluoro-9-chloro-10,11-dihydrodibenzo[b,f]thiepin-11-one:

The mixture of 2.5g of 2-chloro-6-(O-fluorophenylthio-phenylacetic acid and 30g of polyphosphoric acid was stirred at 120° C for 24 hours. After cooling, to the mixture was added icewater and the mixture was extracted with chloroform. The extract was washed with water, saturated sodium carbonate, then water, dried over anhydrous sodium sulfate and freed of the solvent under reduced pressure to obtain the residue. This was recrystallized from diethylether to afford 1.99g (82.6%) of 4-fluoro-9-chloro-10,11-dihydrodibenzo[b,f]thiepin-11-one as colorless needles having a melting point of 128°-130° C.

| IR ($\gamma_{max}^{CHCl_3}$ cm$^{-1}$) : | 1680 (C=O) |
| --- | --- |
| NMR (CDCl$_3$) δ : | 4.58 (2H, s, CH$_2$), |
| | 6.95 -7.60 (5H, m, aromatic protons) |
| | 7.90 (1H, m, C$_1$—H) |
| MS (m/e) : | 278 (M$^+$) |

EXAMPLE 27

9-cyano-4-fluoro-10,11-dihydrodibenzo[b,f]thiepin-11-one hydrazone:

The mixture of 0.55g of 9-cyano-10,01-dihydrodibenzo[b,f]thiepin-11-one, 0.9g of 100% hydrazine hydrate and 30ml of ethanol was heated under reflux on a waterbath for 5 hours. The solvent was evaporated to separate crystals, which were washed with small amount of ethanol, and there was obtained 0.55g of 9-cyano-4-fluoro-10,11-dihydrodibenzo[b,f]thiepin-11-one hydrazone having a melting point of 203°-206° C.

| IR ($\gamma_{max}^{KBr}$ cm$^{-1}$) : | 3400 (NH$_2$), 3240 (NH$_2$), |
| --- | --- |
| | 2240 (CN) |
| NMR [in (CD$_3$)$_2$SO] δ : | 4.35 (2H, s, C$_{10}$—H$_2$), |
| | 6.37 (2H, s, NH$_2$), |
| | 6.80-7.90 (6H, m, aromatic protons) |
| MS (m/e) : | 283 (M$^+$) |

EXAMPLE 28

9-carboxy-4-hydroxy-10,11-dihydrodibenzo[b,f]thiepin:

500mg of 9-cyan0-4-fluoro-10,11-dihydrodibenzo[b,f]thiepin-11-one hydrazone was dissolved in 5ml of diethylene glycol and to this mixture was added 500mg of sodium hydroxide in 5ml of diethylene glycol. The reaction mixture was heated with stirring at 180°-200° C for 2 hours. After cooling, 30ml of water was added to the mixture, which was extracted with benzene. The aqueous layer was acidified with conc. hydrochloric acid, extracted with ethyl acetate and the extract was washed with water and dried over anhydrous sodium sulfate. The solvent was evaporated to obtain glutinous residue, which was chromatographed over silica gel and eluted with benzene-ethyl acetate (1:1). Recrystallization from diluted methanol solution of the crude product obtained from a first fraction afforded 80mg of 9-carboxy-4-hydroxy-10,11-dihydrodibenzo[b,f]thiepin having a melting point of 171°-173° C.

| IR ($\gamma_{max}^{KBr}$ cm$^{-1}$) : | 3400 (OH), 1695 (COOH) |
| --- | --- |
| NMR (in CD$_3$OD) δ : | 3.35, 3.80 (each 2H, two m, C$_{10}$— and C$_{11}$—H$_2$), |
| | 6.60-7.82 (6H, m, aromatic protons) |
| MS (m/e) : | 272 (M$^+$) |

EXAMPLE 29

9-carboxy-4-diethyleneglycoxy-10,11-dihydrodibenzo[b,f]thiepin:

500mg of 9-cyano-4fluoro-10,11-dihydro-dibenzo[b,f]thiepin-11-one hydrazone was dissolved in 5ml of diethylene glycol and to this solution was added 500mg of sodium hydroxide in 5ml of diethylene glycol. The thus obtained mixture was heated with stirring at 180°-200° C for 2 hours. After cooling, 30ml of water was added to the mixture, which was extracted with benzene. The aqueous layer was acidified with conc. hydrochloric acid and extracted with ethyl acetate. The extract was washed with water and dried over anhydrous sodium sulfate. The solvent was evaporated to obtain a glutinous residue, which was chromatographed over silica gel, and eluted benzeneethyl acetate (1:1). Recrystallization from ethyl acetate of the crude product obtained from a second fraction afforded 190mg of 9-carboxy-4-diethylene-glycoxy-10,11-dihydrodibenzo[b,f]thiepin having a melting point of 128°-130° C.

| IR ($\delta_{max}^{KBr}$ cm$^{-1}$) : | 3390 (OH), 1680 (COOH) |
| --- | --- |
| NMR (in CD$_3$OD) δ : | 3.60-4.24 (12H, m, ethylenic and |
| | C$_{10}$ and C$_{11}$—H$_2$ protons), |
| | 6.70 -7.94 (6H, m, aromatic protons) |
| MS (m/e) : | 360 (M$^+$) |

EXAMPLE 30

3-fluoro-9-chloro-10,11-dihydrodibenzo[b,f]thiepin-11-one:

The mixture of 8.0g of 2-chloro-6-(m-fluoro-phenyl-thio)-phenylacetic acid and 80g at polyphosphoric acid was stirred at 120°–125° C for 3 hours. After cooling, to the mixture was added water and the mixture was extracted with chloroform. The extract was washed with 100ml of 1% sodium hydroxide solution, then water, dried over anhydrous sodium sulfate and freed of the solvent to afford 6.2g (83%) of 3-fluoro-9-chloro-10,11-dihydrodibenzo[b,f]thiepin-11-one having a melting point of 109°–111° C.

| | |
|---|---|
| IR ($\gamma_{max}^{KBR}$ cm$^{-1}$) : | 1665 (C=O) |
| NMR (CDCl$_3$) δ : | 8.18 (1H, dd, J=8.5Hz and 6.0Hz, C$_1$—H), |
| | 7.60–6.88 (5H, m, aromatic protons), |
| | 4.58 (2H, s, CH$_2$) |
| MS (m/e) : | 280, 278 (M$^+$) |

EXAMPLE 31

9-cyano-3-fluoro-10,11-dihydrodibenzo[b,f]thiepin-11-one hydrazone:

The mixture of 1.0g of 9-cyano-3-fluoro-10,11-dihydrodibenzo-[b,f]thiepin-11-one, 1.1g of 100% hydrazine hydrate and 16ml of ethanol was heated under reflux for 4.5 hours. The reaction mixture was concentrated to about one-fifth. After cooling, crystals was collected by filtration, there was obtained 9-cyano-3-fluoro-10,11-dihydrodibenzo[b,f]thiepin-11-one hydrazone having a melting point of 178°–179° C in quantitative yield.

| | |
|---|---|
| IR ($\gamma_{max}^{KBr}$ cm$^{-1}$) : | 3400 (NH$_2$), 3240 (NH$_2$) |
| NMR [(CD$_3$)$_2$SO] δ : | 8.00–6.00 (8H, m, aromatic protons and NH$_2$), |
| | 4.30 (2H, s, —CH$_2$—) |
| MS (m/e) : | 283 (M$^+$) |

EXAMPLE 32

9-carboxy-3-fluoro-10,11-dihydrodibenzo[b,f]thiepin and 9-carboxy-3-hydroxy-10,11-dihydrodibenzo[b,f]-thiepin:

To 1.0g of sodium hydroxide dissolved in 15ml of diethylene glycol was added 1.0g of 9-cyano-3-fluoro-10,11-dihydrodibenzo[b,f]thiepin-11-one hydrazone and the resulting mixture was heated with stirring at 190°–200° C for 2 hours. After cooling, water was added to the mixture, which was extracted with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel, and eluted with ethyl acetate-benzene (1:10), and there was obtained the crude product. Recrystallization from methanol afforded 102mg of 9-carboxy-3-fluoro-10,11-dihydrodibenzo[b,f]thiepin having a melting point of 209°–211° C.

| | |
|---|---|
| IR ($\gamma_{max}^{KBr}$ cm$^{-1}$) : | 3100–2400 (COOH), 1670 (CO) |
| NMR [(CD$_3$)$_2$SO] δ : | 3.00–4.00 (4H, m, CH$_2$), |
| | 6.88–7.48 (4H, m, aromatic protons), |
| | 7.56–7.84 (2H, m, aromatic protons) |
| MS (m/e) : | 274 (M$^+$) |

As eluted with ethyl acetate-benzene (1:5), there was obtained 52mg of 9-carboxy-3-hydroxy-10,11-dihydrodibenzo[b,f]-thiepin having a melting point of 219°–221° C (decomposition).

The Rf values and IR spectra → of this product are in accord with those of the compound obtained according to Example 14.

EXAMPLE 33

9-carboxy-3-hydroxy-10,11-dihydrodibenzo[b,f]thiepin:

1.0g of 9-cyano-3-fluoro-10,11-dihydrodibenzo[b,f]-thiepin-11-one hydrazone and 1.0g of sodium hydroxide were added to 15ml of diethylene glycol and the resulting mixture was heated with stirring at 190°–200° C for 5 hours. After cooling, water was added to the mixture, which was washed with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel and eluted with benzene-ethyl acetate (3:2), and there was obtained crude product. Recrystallization from ethanol-water afforded 180mg of 9-carboxy-3-hydroxy-10,11-dihydrodibenzo[b,f]thiepin having a melting point of 219°–221° C.

| | |
|---|---|
| IR ($\gamma_{max}^{KBr}$ cm$^{-1}$) : | 3400–2880 (COOH and OH), |
| | 1690 (CO) |
| NMR (CD$_3$OD) δ : | 7.70 (1H, d, d, J=7.5Hz and 1.0Hz, C$_6$—H or C$_8$—H), |
| | 7.56 (1H, d, d, J=7.5Hz, and 1.0Hz, C$_6$—H or C$_8$—H), |
| | 7.12 (1H, t, J=7.5Hz, C$_7$—H), |
| | 6.84 (1H, d, J=8.0Hz, C$_1$—H), |
| | 6.76 (1H, d, J=2.5Hz, C$_4$—H), |
| | 6.54 (1H, d, d, J=8.0Hz and 2.5Hz, C$_2$—H), |
| | 3.80–3.64 (2H, m, CH$_2$), |
| | 3.32–3.08 (2H, m, CH$_2$) |
| MS (m/e) : | 272 (M$^+$) |

EXAMPLE 34

9-carboxy-3-diethyleneglycoxy-10,11-dihydrodibenzo[b,f]thiepin:

To 15ml of diethylene glycol was added 1.0g of 9-cyano-3-fluoro-10,11-dihydrodibenzo[b,f]thiepin-11-one hydrazone and 1.0g of sodium hydroxide and the resulting mixture was heated with stirring at 190°–200° C for 5 hours. After cooling, water was added to the mixture, which was washed with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel, and eluted with benzene-ethyl acetate (3:2). Recrystallization from methanol-water of the thus obtained product afforded 160mg of 9-carboxy-3-diethyleneglycoxy-10,11-dihydrodibenzo[b,f]-thiepin having a melting point of 125°–128° C.

| | |
|---|---|
| IR ($\gamma_{max}^{KBr}$ cm$^{-1}$) : | 3340 (OH), 3000–2500 (COOH), 1700 (CO) |
| NMR (CD$_3$OD) δ : | 7.60–7.40 (2H, m, C$_6$—H and C$_8$—H), |
| | 7.20 (1H, t, J=7.5Hz, C$_7$—H), |
| | 6.76 (1H, d, J=8.0Hz, C$_1$—H), |
| | 6.72 (1H, d, J=2.5Hz, C$_4$—H), |
| | 6.52 (1H, d, d, J=8.0Hz and 2.5Hz, C$_2$—H), |
| | 4.04–3.00 (12H, m, CH$_2$) |
| MS (m/e) : | 360 (M$^+$) |

EXAMPLE 35

9-carboxy-3-diethyleneglycoxy-10,11-dihydrodibenzo[b,f]thiepin:

To 1.0g of sodium hydroxide dissolved in 15ml of diethylene glycol was added 1.0 g of 9-cyano-3-fluoro-10,11-dihydrodibenzo[b,f]thiepin-11-one hydrazone and the resulting mixture was heated with stirring at 190°-200° C. After cooling, water was added to the mixture, which was washed with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel, and eluted with ethyl acetate-benzene (1:5). Recrystallization from methanol-water of the thus obtained product afforded 150mg of 9-carboxy-3-diethyleneglycoxy-10,11-dihydrodibenzo[b,f]thiepin having a melting point of 125°-128° C.

The Rf values and IR spectra values of Rf and results in IR spectrum of this compound are in accord with those of the compound obtained according to Example 21 (b-1).

EXAMPLE 36

9-carboxy-3-fluoro-10,11-dihydrodibenzo[b,f]thiepin and 9-carboxy-3-hydroxy-10,11-dihydrodibenzo[b,f]-thiepin 5.0g of 9-carboxy-3-fluoro-10,11-dihydrodibenzo[b,f]thiepin-11-one and 5.0g of 100% hydrazine hydrate were dissolved in a mixed solvent of 50ml of ethanol and 50ml of dioxane and the resulting mixture was heated under reflux for 7 hours. After the solvent was evaporated under reduced pressure, the residue was washed with ethanol and to this was added 5g of sodium hydroxide in 150ml of diethylene glycol.

The thus obtained mixture was heated with stirring at 190°-200° C for 2 hours. After cooling, water was added to the mixture, which was washed with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel and eluted with ethyl acetate-benzene (1:10), and there was obtained crude product. Recyrstallization from methanol afforded 800mg of 9-carboxy-3-fluoro-10,11-dihydrodibenzo[b,f]thiepin having a melting point of 208°-210° C.

| Elemental Analysis : as $C_{15}H_{11}SO_2F$ | |
|---|---|
| Calculated (%) : | C: 65.68 H: 4.04 |
| Found (%) : | C: 65.87 H: 3.95 |
| IR ($\gamma_{max}^{KBr}$ cm$^{-1}$) : | 3100-2400 (COOH), 1670 (CO) |
| NMR [(CD$_3$)$_2$SO] δ : | 3.00-4.00 (4H, m, CH$_2$ × 2), |
| | 6.88-7.48 (4H, m, aromatic protons), |
| | 7.56-7.84 (2H, m, aromatic protons) |
| MS (m/e) : | 274 (M$^+$) |

As eluted with ethyl acetate-benzene (1:5), there was obtained 9-carboxy-3-hydroxy-10,11-dihydrodibenzo[b,f]thiepin, which was recrystallized from ethanol-water to give 400mg of the desired product having a melting point of 219°-221° C (decomposition).

| Elemental Analysis : as $C_{15}H_{12}SO_3$ | |
|---|---|
| Calculated (%) : | C: 66.29 H: 4.51 |
| Found (%) : | C: 66.16 H: 4.44 |

| -continued Elemental Analysis : as $C_{15}H_{12}SO_3$ | |
|---|---|
| IR ($\gamma_{max}^{KBr}$ cm$^{-1}$) : | 3400-2880 (COOH, OH), 1690 (CO) |
| NMR (CD$_3$OD) δ : | 3.08-3.32 (2H, m, CH$_2$), |
| | 3.64-3.80 (2H, m, CH$_2$), |
| | 6.54 (1H, d, d, J=8Hz and 2.5Hz, C$_2$—H), |
| | 6.76 (1H, d, J=2.5Hz, C$_4$—H), |
| | 6.84 (1H, d, J=8.0Hz, C$_1$—H), |
| | 7.12 (1H, t, J=7.5Hz, C$_7$—H), |
| | 7.56 (1H, d, d, J=7.5Hz and 1.0Hz, C$_{6-H\ or\ C8}$—H), |
| | 7.00 (1H, d, d, J=7.5Hz and 1.0Hz, C$_6$—H or C$_8$—H) |
| MS (m/e) : | 272 (M$^+$) |

EXAMPLE 37

9-carboxy-3-diethyleneglycoxy-10,11-dihydrodibenzo[b,f]-thiepin:

5.0g of 9-carboxy-3-fluoro-10,11-dihydrodibenzo[b,f]thiepin-11-one and 5.0g of 100% hydrazine hydrate were dissolved in a mixed solvent of 50ml of ethanol and 50ml of dioxane and the resulting mixture was heated under reflux for 7 hours. The solvent was evaporated under reduced pressure to obtain the residue, which was washed with ethanol. To this was added 5g of sodium hydroxide dissolved in 150ml of diethylene glycol and the resulting mixture was heated with stirring at 190°-200° C for 2 hours. After cooling, water was added to the reaction mixture, which was washed with benzene. The aqueous layer was acidified with hydrochloric acid and extracted with ethyl acetate. The extract was washed with water and dried over anhydrous sodium sulfate. The solvent was evaporated to obtain the residue, which was chromatographed over silica gel, and eluted with ethyl acetate-benzene (1:5). Recrystallization from methanol-water of the thus obtained product afforded 1.2g of 9-carboxy-3-diethyleneglycoxy-10,11-dihydrodibenzo[b,f]thiepin having a melting point of 125°-128° C.

| Elemental Analysis : as $C_{19}H_{20}SO_5$ | |
|---|---|
| Calculated (%) : | C: 63.33 H: 5.59 |
| Found (%) : | C: 63.58 H: 5.42 |
| IR ($\gamma_{max}^{KBr}$ cm$^{-1}$) : | 3340 (OH), 3000-2500 (COOH), 1700 (CO) |
| NMR (in CD$_3$OD) δ : | 3.00-4.04 (12H, m, CH$_2$ × 6), |
| | 6.52 (1H, d, d, J=8.0Hz and 2.5Hz, C$_2$—H), |
| | 6.72 (1H, d, J=2.5Hz, C$_4$—H), |
| | 6.76 (1H, d, J=8.0Hz, C$_1$—H), |
| | 7.20 (1H, t, J=7.5Hz, C$_7$—H), |
| | 7.40 -7.60 (2H, m, C$_6$—H and C$_8$—H) |
| MS (m/e) : | 360 (M$^+$) |

EXAMPLE 38

9-carboxy-4-hydroxy-10,11-dihydrodibenzo[b,f]thiepin:

5.0g of 9-carboxy-4-fluoro-10,11-dihydrodibenzo[b,f]thiepin-11-one and 5.0g of 100% hydrazine hydrate were dissolved in the mixed solvent of 50ml of ethanol and 50ml of dioxane. The resulting mixture was heated under reflux for 5 hours. The solvent was evaporated under reduced pressure to obtain the residue, which was washed with ethanol. To this was added 5.0g of sodium hydroxide in 100ml of diethylene glycol and the resulting mixture was heated with stirring at 180°-200° C for 2 hours. After cooling, water was added to the mixture, which was extracted with benzene. The aqueous layer was acidified with hydrochloric acid and extracted with ethyl acetate. The extract was washed with water and dried over anhydrous sodium sulfate. The solvent was evaporated to obtain a glutinous residue which was chromatographed over silica gel, and eluted with benzene-ethyl acetate (1:1). Recrystallization of the thus obtained crude product from methanol-water afforded 600mg of 9-carboxy-4-hydroxy-10,11-dihydrodibenzo-[b,f]thiepin having a melting point of 171°-173° C.

| Elemental Analysis : as $C_{15}H_{12}SO_3$ | |
|---|---|
| Calculated (%): | C: 66.16 H: 4.44 |
| Found (%): | C: 66.01 H: 4.39 |
| IR ($\gamma_{max}^{KBr}$ cm$^{-1}$): | 3400 (OH), 1695 (COOH) |
| NMR (in CD$_3$OD)δ: | 3.35, 3.80 (each 2H, two m, C$_{10}$— and C$_{11}$—H$_2$), |
| | 6.60-7.82 (6H, m, aromatic protons) |
| MS (m/e): | 272 (M$^+$) |

EXAMPLE 39

9-carboxy-4-diethyleneglycoxy-10,11-dihydrodibenzo[b,f]-thiepin:

5.0g of 9-carboxy-4-fluoro-10,11-dihydrodibenzo[b,f]thiepin-11-one and 5.0g of 100% hydrazine hydrate were dissolved in the mixed solvent of 50ml of ethanol and 50ml of dioxane and the resulting mixture was heated under reflux for 5 hours. The solvent was evaporated under reduced pressure to obtain the residue, which was washed with ethanol. To this was added 5.0g of sodium hydroxide dissolved in 100ml of diethylene glycol and the resulting mixture was heated with stirring at 180°-200° C for 2 hours. After cooling, water was added to the mixture, which was extracted with benzene. The aqueous layer was acidified with hydrochloric acid and extracted with ethyl acetate. The extract was washed with water and dried over anhydrous sodium sulfate. The solvent was evaporated to obtain a glutinous residue, which was chromatographed over silica gel, and eluted with benzene-ethyl acetate (1:1). Recrystallization from ethyl acetate of the thus obtained crude product afforded 1.3g of 9-carboxy-4-diethyleneglycoxy-10,11-dihydrodibenzo[b,f]thiepin having a melting point of 128°-130° C.

| Elemental Analysis : as $C_{19}H_{20}SO_5$ | |
|---|---|
| Calculated (%) : | C: 63.33 H: 5.59 |
| Found (%) : | C: 63.58 H: 5.49 |
| IR ($\gamma_{max}^{KBr}$ cm$^{-1}$) : | 3390 (OH), 1680 (COOH) |
| NMR (in CD$_3$OD) δ : | 3.60-4.24 (12H, m, ethylenic protons and C$_{10}$ and C$_{11}$—H$_2$), |
| | 6.70-7.94 (6H, m, aromatic protons) |
| MS (m/e) : | 360 (M$^+$) |

EXAMPLE 40

2-trifluoromethyl-9-chloro-10,11-dihydrodibenzo[b,f]thiepin-11one:

The mixture of 5.6g of 2-chloro-6-(p-trifluoromethylphenylthio)phenylacetic acid and 56g of polyphosphoric acid was stirred at 130°-140° C for 4 hours. After cooling, to the mixture was added ice and the mixture was extracted with benzene-ethyl acetate. The extract was washed with water, 2% sodium hydroxide solution, then water, dried over anhydrous sodium sulfate and freed of the solvent under reduced pressure to obtain 1.7g of crystals. They were chromatographed on silica gel, and eluted with benzene, there was obtained 1.4g (25.6%) of 2-trifluoromethyl-9-chloro-10,11-dihydrodibenzo[b,f]thiepin-11-on as pale yellow crystals having a melting point of 105°-107.5° C.

IR ($\gamma_{max}^{CHCl_3}$ cm$^{-1}$) : 1690 (C=O), 1320 (CF$_3$)
NMR (CDCl$_3$) δ :
4.70 (2H, s, —CO—CH$_2$—),
7.10-7.92 (5H, m, aromatic protons),
8.54 (1H, s, aromatic proton)
MS (m/e) : 330, 328 (M$^+$)

EXAMPLE 41

2-trifluoromethyl-9-chloro-10,11-dihydrodibenzo[b,f]thiepin-11-ol:

To the mixture of 2-trifluoromethyl-9-chloro-10,11-dihydrodibenzo[b,f]thiepin-11-one obtained in Example 40 and 10ml of methanol was gradually added 0.2g of sodium boron hydride with ice-cooling over a period of 5 minutes and the mixture was reacted at room temperature for 30 minutes and refluxed for 15 minutes. After the completion of the reaction, methanol was distilled off. After cooling, to the mixture was added water and the mixture was extracted with chloroform. The extract was washed with water, dried over anhydrous sodium sulfate and freed of the solvent to obtain 0.5g of 2-trifluoromethyl-9-chloro-10,11-dihydrodibenzo[b,f]thiepin-11-ol as colorless crystals having a melting point of 130°-132° C.

IR ($\gamma_{max}^{CHCl_3}$ cm$^{-1}$) : 3600 (OH), disappearance of absorption due to C=O
NMR (CDCl$_3$) δ : 2.38 (1H, d, OH),
3.68 (2H, m, —CH$_2$—),
5.50 (1H, d, >CH—OH),
6.92-7.90 (6H, m, aromatic protons)
MS (m/e) : 330, 332 (M$^+$)

EXAMPLE 42

2-trifluoromethyl-9-chloro-11-chloro-10,11-dihydrodibenzo-[b,f]thiepin:

To the mixture of 0.5g of 2-trifluoromethyl-9-chloro-10,11-dihydrodibenzo[b,f]thiepin-11-ol, 5ml of anhydrous benzene and one drop of anhydrous pyridine were added dropwise with stirring 0.3g of thionyl chloride with ice-cooling and the resulting mixture was reacted at room temperature for 10 minutes, then refluxed for 20 minutes, and freed of benzene under reduced pressure. To the thus obtained residue was added water and the mixture was extracted with benzene. The extract was washed with water, saturated soidum bicarbonate, then water, dried over anhydrous sodium sulfate and freed of benzene to obtain 2-trifluoromethyl-9-chloro-11-chloro-10,11-dihydrodibenzo[b,f]-thiepin as colorless crystals having a melting point of 88°-90° C.

IR ($\gamma_{max}^{CHCl_3}$ cm$^{-1}$) : disappearance of absorption due to OH
NMR (CCl$_4$) δ :
3.94-4.20 (2H, m, —CH$_2$—),
5.68-5.90 (1H, m, >CH—Cl),
6.96-7.90 (6H, m, aromatic protons)
MS (m/e) : 348, 350 (M$^+$)

EXAMPLE 43

2-trifluoromethyl-9-chloro-10,11-dihydrodibenzo[b,f]thiepin:

To the mixture of 0.2g of lithium aluminum hydride and 20ml of anhydrous tetrahydrofuran was added with stirring under ice-cooling 400mg of 2-trifluoromethyl-9-chloro-11-chloro-10,11-dihydrodibenzo[b,f]thiepin dissolved in 10ml of anhydrous tetrahydrofuran. Thereafter, the mixture was reacted under cooling for 0.5 hr. at the room temperature and further under reflux condition for 3.5 hrs. After cooling, to the mixture was added water with stirring under cooling to decompose an excess of lithium aluminum hydroxide and the resulting mixture was filtered with the use of celite. The filtrate was extracted with chloroform, chloroform layer was washed with water and dried over anhydrous sodium sulfate. The solvent was evaporated to obtain 372ml of an oily substance, which was chromatographed on a silica gel, eluted with n-hexane, and there was obtained 65mg of 2-trifluoromethyl-9-chloro-10,11-dihydrodibenzo[b,f]thiepin.

NMR (CCl$_4$) δ : 3.20 –3.60 (4H, m, methylene protons),
6.90–7.64 (6H, m, aromatic protons)
MS (m/e) : 314, 316 (M$^+$)

EXAMPLE 44

2-trifluoromethyl-9-chloro-10,11-dihydrodibenzo[b,f]thiepin-11-hydrazone:

The mixture of 200mg of 2-trifluoromethyl-9-chloro-10,11-dihydrodibenzo[b,f]thiepin-11-one, 0.8ml of hydrazine hydrate, 2ml of ethanol and 2ml of dioxane was refluxed for 20 hours. After the completion of the reaction, the mixture was freed of the solvent under reduced pressure and there was obtained 220mg of 2-trifluoromethyl-9-chloro-10,11-dihydrodibenzo[b,f]thiepin-11-hydrazone as colorless crystals. This was recrystallized from ethanol to give colorless needles having a melting point of 139.5°–141.5° C.

IR (γ $_{max}^{CHCl_3}$ cm$^{-1}$) : 3420 (NH$_2$)
NMR (CDCl$_3$) δ :

4.28 (2H, s, 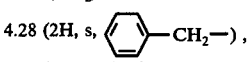—CH$_2$—), 5.94 (2H, s, NH$_2$),
7.00–7.58 (6H, m, aromatic protons),
8.22 (1H, s, aromatic proton)
MS (m/e) : 342, 344 (M$^+$)

EXAMPLE 45

2-trifluoromethyl-9-chloro-10,11-dihydrodibenzo[b,f]thiepin:

The mixture of 61mg of 2-trifluoromethyl-9-chloro-10,11-dihydrodibenzo[b,f]thiepin-11-hydrazone and 2ml of diethylene glycol was stirred at 180°–200° C for 2.5 hours. After cooling, to te mixture was added water and the mixture was extracted with chloroform. The extract was washed with water, dried over anhydrous sodium sulfate and freed of the solvent to obtain 57mg of a brown oil. This was chromatographed on silica gel and eluted with n-hexane, and there was obtained 2-trifluoromethyl-9-chloro-10,11-dihydrodibenzo[b,f]thiepin.

NMR (CCl$_4$) δ : 3.20–3.60 (4H, m, methylene protons),
6.94–7.64 (6H, m, aromatic protons)
MS (m/e) : 314, 316 (M$^+$)

EXAMPLE 46

2-trifluoromethyl-9-cyano-10,11-dihydrodibenzo[b,f]thiepin:

The mixture of 450mg of 2-trifluoromethyl-9-chloro-10,11-dihydrodibenzo[b,f]thiepin, 0.4g of copper cyanide, 0.05g of anhydrous copper sulfate and 10ml of N-methylpyrrolidone was stirred at 180° to 210° C for 18.5 hrs. while preventing the moisture. A ter cooling, to the mixture was added 2.5ml of conc. ammonia water and 35ml of water and the resulting mixture was filtered with the use of celite. The thus obtained solution was extracted with benzene and the extract was washed with water and dried over anhydrous sodium sulfate. The solvent was evaporated to obtain 0.3g of a brown oily substance, which was chromatographed on a silica gel, eluted with n-hexane, and there was obtained 64mg of the desired product. This was recrystallized from n-hexane to afford 2-trifluoromethyl-9-cyano-10,11-dihydrodibenzo-[b,f]thiepin having a melting point of 113° to 114.5° C as colorless crystals.

IR (γ $_{max}^{CHCl_3}$ cm$^{-1}$): 2230 (CN)
NMR (CCl$_4$) δ : 3.36–3.80 (4H, m, methylene protons),
7.10–7.90 (6H, m, aromatic protons)
MS (m/e) : 305 (M$^+$)

EXAMPLE 47

2-trifluoromethyl-10,11-dihydrodibenzo[b,f]thiepin-9-carboxylic acid:

To 1g of potassium hydroxide dissolved in 1ml of water and 4ml of ethanol was added 106mg of 2-trifluoromethyl-9-cyano-10,11-dihydrodibenzo[b,f]thiepin and the resulting mixture was refluxed for 24 hrs. After cooling, to this was added 4% sodium hydroxide solution and ether. After shaking, the aqueous layer was separated, acidified by adding conc. hydrochloric acid and extracted with chloroform. Extract was washed with water and dried over anhydrous sodium sulfate. The solvent was evaporated to obtain 87 mg (77.3% of yield) of the desired product as colorless powder. This was recrystallized from the mixed solvent of benzene and n-hexane to afford 2-trifluoromethyl-10,11-dihydrodibenzo[b,f]thiepin-9-carboxylic acid having a melting point of 178.5° to 179.5° C as colorless crystals.

IR (γ $_{max}^{KBr}$ cm$^{-1}$) : 3400–2400 (COOH), 1680 (CO)
NMR (CDCl$_3$) δ : 3.40–3.60 (2H),
3.84–4.16 (2H, methylene protons),
7.20–8.20 (7H, m, aromatic + COOH protons)
MS (m/e) : 324 (M$^+$)

EXAMPLE 48

2-trifluoromethyl-9-(N,N-diisopropyhyl)aminocarbonyl-10,11-dihydrodibenzo[b,f]thiepin:

The mixture of 119mg of 2-trifluoromethyl-9-carboxy-10,11-dihydrodibenzo[b,f]thiepin, 6ml of anhydrous benzene and 0.2ml of thionyl chloride was refluxed with stirring for about 5 hours, and then freed of the solvent under reduced pressure. To the residue was added 6ml of anhydrous benzene and 374mg of diisopropylamine and the mixture was stirred at room temperature for 15 hours, then refluxed with stirring for 3 hours. Benzene was evaporated and to the residue was added water. The resulting mixture was extracted with chloroform. The extract was washed with water, saturated sodium chloride solution, dried over anhydrous sodium sulfate and freed of the solvent to give 167mg of the residue. This was chromatographed over silica gel, and eluted with chloroform, there was obtained 88mg of a colorless glutinous substance.

This was recrystallized fron n-hexane and there was obtained 88mg (59%) of 2-trifluoromethyl-9-(N,N-diisopropyl)aminocarbonyl-10,11-dihydrodibenzo[b,f]-thiepin as colorless crystals having a melting point of 121.5°–122.5° C.

IR ($\gamma_{max}^{KBr}$ cm$^{-1}$) : 1620 C=O)
NMR (CDCl$_3$) δ : 0.92–1.20 (6H, m, CH$_3$ ×2),
1.40–1.52 (6H, m, CH$_3$ × 2),
3.00–3.76 (6H, m, —CH$_2$CH$_2$—
+ CH × 2),
6.84–7.62 (6H, m, aromatic protons)
MS (m/e) : 407 (M$^+$)

EXAMPLE 49

2-trifluoromethyl-9-(β-hydroxyethylpiperazinyl)carbonyl-10,11-dihydrodibenzo[b,f]thiepin:

The mixture of 100mg of 2-trifluoromethyl-9-carboxy-10,11-dihydrodibenzo[b,f]thiepin, 5ml of anhydrous benzene and 0.3ml of thionyl chloride was refluxed for about 4 hours and, after cooling, freed of the solvent under reduced pressure to obtain the residue. This residue was added to the mixture of 40.5mg of piperazine ethanol, 31.9mg of triethylamine and 5ml of chloroform, and the resulting mixture was stirred at room temperature for about 23 hours. The mixture was extracted with chloroform and the extract was washed with saturated sodium bicarbonate, saturated sodium chloride solution, dried over anhydrous sodium sulfate and freed of chloroform to obtain 18mg of glutinous substance. This was chromatographed over silica gel and eluted with chloroform, there was obtained 117mg (87%) of colorless gluitinous substance.

This was made hydrochloride and recrystallized from methanoldiethyl ether to give 2-trifluoromethyl-9-(β-hydroxyethylpiperazinyl)carbonyl-10,11-dihydrodibenzo[b,f]thiepin as colorless crystals having a melting point of 248°–250° C.

IR ($\gamma_{max}^{KBr}$ cm$^{-1}$) : 3600–3200 (OH), 1620 (C=O)
NMR (CDCl$_3$) δ0 : 2.24–2.80 (7H, m, methylene protons),
3.80–3.40 (6H, m, methylene protons), 3.48–3.68 (2H, t, J=6Hz, 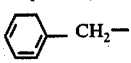 CH$_2$—), 3.68–3.92 (2H, t, J=6Hz, 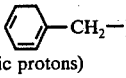—CH$_2$—), 7.00–7.52 (6H, m, aromatic protons)
MS (m/e) : 436 (M$^+$)

EXAMPLE 50

2-ethoxy-9-chloro-10,11-dihydrodibenzo[b,f]thiepin-11-one:

The mixture of 3g of 2-chloro-6-(p-ethoxyphenylthio)-phenylacetic acid was stirred at 80°–90° C. After cooling, to the mixture was added 300g of ice-water and the resulting mixture was extracted with chloroform. The extract was washed with water, 5% sodium bicarbonate solution, then water, dried over anhydrous sodium sulfate and freed of the solvent to give the residue. This residue was recrystallized from benzene-n-hexane to afford 1.2g (54%) of 2-ethoxy-9-chloro-10,11-dihydrodibenzo[b,f]thiepin-11-one as pale brown powdered crystalls having a melting point of 121°–123° C.

IR ($\gamma_{max}^{CHCl_3}$ cm$^{-1}$) : 1675 (C=O)
NMR (CDCl$_3$) δ : 1.36 (3H, t, J=7Hz, CH$_3$—CH$_2$),
4.00 (2H, q, J=7Hz, CH$_3$—CH$_2$), 4.62 (2H, s, 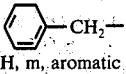—CH$_2$—), 6.80–7.70 (6H, m, aromatic protons)
MS (m/e) : 304 (M$^+$)

EXAMPLE 51

2-ethoxy-9-chloro-10,11-dihydrodibenzo[b,f]thiepin-11-ol:

An amount of 31.8g of 2-ethoxy-9-chloro-10,11-dihydrodibenzo-[b,f]thiepin-11-one was dissolved in 200ml of a mixed solvent of methanol and chloroform (5/1) and the mixture was stirred at room temperature for 2 hours and freed of the solvent to obtain the residue. To the resulting residue was added 100ml of water and the mixture was extracted with chloroform. The extract was washed with water, dried over anhydrous sodium sulfate and freed of the solvent to obtain the residue.

This residue was recrystallized from benzene-n-hexane to obtain 1.6g (89%) of 2-ethoxy-9-chloro-10,11-dihydrodibenzo-[b,f]thiepin-11-ol as colorless powdered crystals having a melting point of 88°–90 ° C.

IR ($\gamma_{max}^{CHCl_3}$ cm$^{-1}$) : 3600 (OH)
MS (m/e): 306 (M$^+$)

EXAMPLE 52

9-chloro-10,11-dihydro-2-ethoxydibenzo[b,f]thiepin:

The mixture of 1.1g of 9-chloro-10,11-dihydro-2-ethoxy-11-hydroxydibenzo[b,f]thiepin and 30ml of thionyl chloride was refluxed for 3 hrs. and evaporated to obtain the residue, to which was added 50g of ice-water. The resulting mixture was extracted with chloroform and the extract was washed with water and dried over calcium chloride. The solvent was evaporated to obtain the concentrated which was added with stirring at room temperature to a mixture of 70ml of anhydrous tetrahydrofuran and 400mg of lithium aluminum hydride. The thus obtained mixture was refluxed with stirring for 4hrs., to which was added 30% sodium hydroxide solution with stirring under cooling with a mixture of ice and sodium chloride. The mixture was filtered and the filtrate was evaporated to obtain the residue, to which was added 100ml of chloroform and 100ml of water, and the chloroform layer was collected. This was washed with water, dried and the solvent was evaporated to obtain 520mg of 9-chloro-10,11-dihydro-2-ethoxydibenzo[b,f]thiepin as oily substance.

NMR (CDCl$_3$) δ : 1.34 (3H, t, J=8Hz, CH$_3$CH$_2$),
3.30 (4H, s, Ar—CH$_2$CH$_2$—Ar),
3.90 (2H, q, J=8Hz, CH$_3$CH$_2$O),
6.48 –7.32 (6H, m, aromatic protons)
MS (m/e) : 290 (M$^+$)

EXAMPLE 53

9-cyano-10,11-dihydro-2-ethoxydibenzo[b,f]thiepin:

The mixture of 520mg of 9-chloro-10,11-dihydro-2-ethoxydibenzo-[b,f]thiepin, 0.1g of copper sulfate, 1g of copper cyanide and 20ml of N-methylpyrrodlidone was refluxed with stirring for 15hrs., while preventing the moisture with calcium chloride. After cooling, to this was added 20ml of conc. ammonia water and 100ml of water, and the mixture was extracted. The extract was washed with water, dried over anhydrous potassium carbonate and, the solvent was evaporated to obtain the residue. This was chromatographed on silica gel, eluted with the mixed solvent of benzene and n-hexane (4:1) and there was otained 150mg of 9-cyano-10,11-dihydro-2-ethoxydibenzo[b,f]thiepin having a melting point of 124° to 126° C as colorless powdered crystals.

| IR ($\gamma_{max}^{CHCl_3}$ cm$^{-1}$) : | 2230 (CN) |
|---|---|
| NMR (CDCl$_3$) : | 1.40 (3H, t, J=7Hz, CH$_3$CH$_2$O), |
| | 3.30–3.60 (4H, m, Ar—CH$_2$CH$_2$—Ar), |
| | 4.00 (2H, q, J=7Hz, CH$_3$CH$_2$O), |
| | 6.60–7.70 (6H, m, aromatic protons) |

EXAMPLE 54

2-ethoxy-10,11-dihydrodibenzo[b,f]thiepin-9-carboxylic acid:

The mixture of 50mg of 9-cyano-10,11-dihydro-2-ethoxydibenzo[b,f]thiepin, 2g of potassium hydroxide, 2ml of water and 10ml of ethanol was refluxed at 45 hrs., and the solvent was evaporated to obtain a concentrate, which was acidified by adding 10% hydrochloric acid and extracted with chloroform. The extract was washed with water, dried over anhydrous sodium sulfate, and the solvent was evaporated to obtain 45mg of solid. This was recrystallized from benzene n-hexane to afford 2-ethoxy-10,11-dihydrodibenzo[b,f]thiepin-9-carboxylic acid having a melting point of 165° to 167° C as colorless powdered crystals.

| IR ($\gamma_{max}^{CHCl_3}$ cm$^{-1}$) : | 1690 (CO) |
|---|---|
| NMR (CDCl$_3$) δ : | 1.38 (3H, t, J=7Hz, CH$_3$CH$_2$O), |
| | 3.30–3.48 (4H, m, Ar—CH$_2$CH$_2$—Ar) |
| MS (m/e) : | 300 (M$^+$) |

EXAMPLE 55

2-methoxy-9-chloro-10,11-dihydrodibenzo[b,f]thiepin-11-one:

The mixture of 30g of 2-chloro-6-(p-methoxyphenylthio)-phenylacetic acid and 300g of polyphosphoric acid was stirred at 110° C for 3 hours. After cooling, to the mixture was added water and the mixture was extracted with chloroform. The extract was washed with 1N sodium hydroxide solution, saturated sodium chloride solution, dried over anhydrous sodium sulfate and freed of the solvent to afford 22.9g (81%) of 2-methoxy-9-chloro-10,11-dihydrodibenzo[b,f]thiepin-11-one as reddish crystals having a melting point of 117°–120° C.

| IR ($\gamma_{max}^{KBr}$ cm$^{-1}$) : | 1680 (C=O) |
|---|---|
| NMR (CDCl$_3$) δ : | 3.72 (3H, s, —OCH$_3$), |
| | 4.56 (2H, s, —CH$_2$—), |
| | 6.80–7.80 (6H, m, aromatic protons) |

EXAMPLE 56

2-methoxy-9-chloro-10,11-dihydrodibenzo[b,f]thiepin-11-hydrazone:

An amount of 20.0g of 2-methoxy-9-chloro-10,11-dihydrodibenzo[b,f]thiepin-11-one was dissolved in the mixed solvent of 200ml of ethanol and 200ml of dioxane and to the mixture was added 30.0g of hydrazine hydrate.

The resulting mixture was refluxed for 20 hours and, after cooling, freed of the solvent to obtain the residue. This residue was recrystallized from ethanol to afford 12.6g (60%) of 2-methoxy-9-chloro-10,11-dihydrodibenzo[b,f]thiepin-11hydrazone as pale yellow cyrstals having a melting point of 116°–119° C.

IR $\gamma_{max}^{KBr}$ cm$^{-1}$) : 3220, 3340 (NH$_2$)

EXAMPLE 57

2-methoxy-9-chloro-10,11-dihydrodibenzo[b,f]thiepin:

An amount of 12.5g of sodium hydroxide was dissolved in 250ml of diethylene glycol by application of heat and to the resulting solution was added 12.5g of 2-methoxy-9-chloro-10,11-dihydrodibenzo[b,f]thiepin-11-hydrazone and the mixture was stirred at 150° C for 4 hours. After cooling, to the mixture was added water and the mixture was extracted with ethyl acetate. The extract was washed with saturated sodium chloride solution, dried over anhydrous sodium sulfate and freed of the solvent to obtain 12.0g of brown oil. This residue was chromatographed over a silica gel and eluted with benzene-n-hexane (1/1), and there was obtained 10.9g (96) of 2-methoxy-9-chloro10,11-dihydrodibenzo[b,f]thiepin as chlorless prismatic crystals having a melting point of 73°–74° C.

| NMR (CDCl$_3$) δ : | 3.61 (4H, s, —CH$_2$CH$_2$—), |
|---|---|
| | 3.80 (3H, s, OCH$_3$), |
| | 6.60–7.46 (6H, m, aromatic protons) |

EXAMPLE 58

2-methoxy-9-cyano-10,11-dihydrodibenzo[b,f]thiepin:

To 100 ml of N-methylpyrrolidone was added 10.8g of 2-methoxy-9-chloro-10,11-dihydrodibenzo[b,f]thiepin, 10.7g of copper cyanide and 0.4g of anhydrous copper sulfate and the resulting mixture was stirred at 190°–195° C for 15 hours. After cooling, to the mixture was added 28% ammonia water, 200 ml of water and 200 ml of benzene and the resulting mixture was shaked and filtered with celite. The filtrate was extracted with benzene. The extract was washed with saturated sodium chloride solution, dried over anhydrous sodium sulfate and freed of the solvent to obtain 9.0g of light brown cyrstals. This product was chromatographed over silica gel and eluted with benzene, there was obtained 5.4g (50%) of 2-methoxy-9-cyano-10,11-dihydrodibenzo[b,f]thiepin as colorless prismatic crystals having a melting point of 129°–130° C.

| IR ($\gamma_{max}^{KBr}$ cm$^{-1}$): | 2215 (CN) |
|---|---|
| NMR (CDCl$_3$) δ : | 3.24 –3.54 (4H, m, —CH$_2$CH$_2$—) |
| | 3.73 (3H, s, OCH$_3$) |
| | 6.50–7.60 (6H,m,aromatic protons) |
| MS (m/e) : | 267 (M$^+$) |

EXAMPLE 59

2-hydroxy-9-carboxy-10,11-dihydrodibenzo[b,f]thiepin.

An amount of 2.2g of sodium hydroxide was dissolved in 30ml of diethylene glycol by application of heat and to the mixture was added 2.2g of 2-methoxy-9-cyano-10,11-dihydrodibenzo[b,f]thiepin and the resulting mixture was stirred at 200° C for 16 hours. After cooling, to the mixture was added water and the mixture was extracted with ethyl acetate. The equeous layer was acidified with conc. hydrochloric acid and extracted with ethyl acetate. This extract was washed with saturated sodium chloride solution, dried over anhydrous sodium sulfate and freed of the solvent to obtain the residue. This residue was recrystallized from benzene to afford 1.1g (46%) of 2-hydroxy-9-carboxy-10,11-dihydrodibenzo[b,f]thiepin as brown crystals having a melting point of 210°–211° C.

EXAMPLE 60

2-methoxy-9-carboxy-10,11-dihydrodibenzo[b,f]thiepin.

An amount of 6.0g potassium hydroxide was dissolved in 20ml of 80% ethanol and to the solution was added 1g of 2-methoxy-9-cyano-10,11-dihydrodibenzo[b,f]thiepin and the resulting mixture was refluxed for 26 hours. The mixture was freed of the solvent under reduced pressure to obtain the residue, which was dissolved in water and extracted with ethyl acetate. The aqueous layer was acidified with conc. hydrochloric acid and extracted with ethyl acetate. The extract was washed with saturated sodium chloride solution, dried over anhydrous sodium sulfate and freed of the solvent to give 743 mg (69%) of 2-methoxy-9-carboxy-10,11-dihydrodibenzo[b,f]thiepin as pale reddish needles having a melting point of 185°–186° C.

| | |
|---|---|
| IR ($\gamma_{max}^{KBr}$ cm$^{-1}$) : | 1690 (C=O) |
| NMR [(CD$_3$)$_2$SO] $\delta$ : | 3.14–3.36 (2H,m,—CH$_2$—) |
| | 3.52–3.76 (5H,m,—CH$_2$— +OCH$_3$) |
| | 6.54–6.75, 7.08–7.30, 7.53–7.72 |
| | (each 2H, all m, aromatic protons) |
| MS (m/e) : | 286 (M$^+$) |

EXAMPLE 61

2-fluoro-9-chloro-10,11-dihydrodibenzo[b,f]thiepin:

0.7g of lithium aluminum hydride was suspended in 20ml of tetrahydrofuran, to the resulting suspension was added dropwise with stirring 2.1g of 9-chloro-11-chloro-2-fluoro-10,11-dihydrodibenzo[b,f]thiepin dissolved in 10ml of anhydrous tetrahydrofuran and the mixture was stirred at room temperature for 0.5hr., further under reflux condition for 3.5 hrs., while preventing the moisture. After completion of the reaction, an excess of lithium aluminum hydride was decomposed by adding ethanol and water, and filtered off using celite. The filtrate was evaporated to obtain the residue, which was chromatographed on silica gel, eluted with chloroform, and there was obtained 1.2g(67.0% of yield) of 2-fluoro-9-chloro-10,11-dihydrodibenzo[b,f]thiepin as pale green viscous oily substance.

| | |
|---|---|
| NMR (CDCl$_3$) $\delta$ : | 3.30 (4H,s,methylene protons due to C$_{10}$ and C$_{11}$ protons) |
| MS (m/e) | : 266, 264 (M$^+$) |

EXAMPLE 62

2-fluoro-9-cyano-10,11-dihydrodibenzo[b,f]thiepin:

The mixture of 5.5g of 2-fluoro-9-chloro-10,11-dihydrodibenzo[b,f]thiepin, 5.4g copper cyanide, 0.6g of anhydrous copper sulfate and 100ml of N-methylpyrrolidone was refluxed overnight at 200° to 210° C while preventing the moisture.

After cooling, to the reaction mixture was added 5ml of conc. ammonia water and 70ml of water, the resulting mixture was extracted with benzene, the extract was washed with water and dried over anhydrous sodium sulfate. The solvent was evaporated to obtain the residue, which was chromatographed on silica gel, eluted with chloroform and there was obtained 1.2g (44.4% of yield) of 2-fluoro-9-cyano-10,11-dihydrodibenzo[b,f]thiepin as pale yellow crystals.

| | |
|---|---|
| IR ($\gamma_{max}^{CHCl_3}$ cm$^{-1}$) | : 2220 (CN) |
| NMR (CDCl$_3$)$\delta$ | : 3.40–3.63 (4H,m,methylene protons due to C$_{10}$ and C$_{11}$ protons) |
| MS (m/e) | : 255 (M$^+$) |

EXAMPLE 63

2-fluoro-10,11-dihydrodibenzo[b,f]thiepin-9-carboxylic acid:

The mixture of 1.0g of 2-fluoro-9-cyano-10,11-dihydrodibenzo[b,f]thiepin, 6g of potassium hydroxide and 20ml of 80% ethanol was refluxed with stirring overnight. After the completion of the reaction, the mixture was concentrated to obtain the residue which was dissolved in 100ml of water. The resulting solution was extracted with diethyl ether-benzene (1:1) and the aqueous layer was acidified with conc. hydrochlonic acid and extracted with ethyl acetate. The extract was washed with water and dried over anhydrous sodium sulfate. The solvent was evaporated to obtain 0.9g of brown solid, which was recrystallized twice from benzene, and there was obtained 0.4g (40.0% of yield) of 2-fluoro-10,11-dihydrodibenzo[b,f]thiepin-9-carboxylic acid having a melting point of 200° to 202° C as pale brown needles.

| | |
|---|---|
| IR ($\gamma_{max}^{KBr}$ cm$^{-1}$) | : 1680 (CO) |
| NMR[(CD$_3$)$_2$SO]$\delta$ | : 3.30–3.47 (2H,m,C$_{11}$—H$_2$) |
| | 3.65–3.82 (2H,m,C$_{10}$—H$_2$) |
| | 6.98–7.92 (6H,m,aromatic protons) |
| MS (m/e) | : 274 (M$^+$) |

What is claimed is:

1. A compound of the following formula:

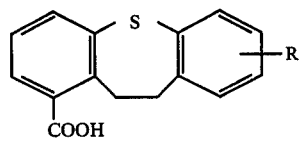

wherein R represents a hydrogen or fluorine atom, a trifluoromethyl, 1–5C lower alkoxy, hydroxy, hydroxyethoxy or aminoethoxy group, or the group of the formula —OCH$_2$CH$_2$OCH$_2$CH$_2$OH.

2. A compound of the following formula:

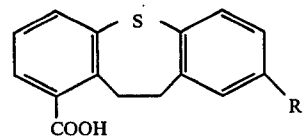

wherein R is defined in claim 1.
3. A compound of the formula

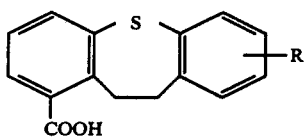

wherein R is the group —OCH$_2$CH$_2$OCH$_2$CH$_2$OH.
4. A compound according to claim 2, wherein R is a fluorine atom.
5. A compound according to claim 2, wherein R is a 1-5C lower alkoxy group.
6. A compound according to claim 2, wherein R is a hydroxy group.
7. A compound of the formula

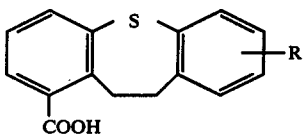

wherein R is a hydroxyethoxy group.
8. A compound of the formula

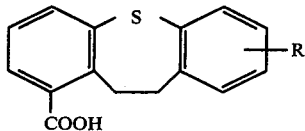

wherein R is an aminoethoxy group.
9. A compound according to claim 1, wherein R is a hydrogen atom.
10. A compound according to claim 1, wherein R is a fluorine atom.
11. A compound according to claim 1, wherein R is a 1-5C lower alkoxy group.
12. A compound according to claim 1, wherein R is a trifluoromethyl group.
13. A compound according to claim 1, wherein R is a hydroxy group.
14. 9-carboxy-2-diethyleneglycoxy-10,11-dihydrodibenzo-[b,f]thiepin.
15. 9-carboxy-2-trifluoromethyl-10,11-dihydrodibenzo[b,f]-thiepin.
16. A pharmaceutical composition comprising an antiinflammatorily effective amount of a compound according to claim 1 in the presence of a pharmaceutically acceptable inert carrier.

* * * * *